United States Patent [19]

Chambers et al.

[11] Patent Number: 5,556,969
[45] Date of Patent: Sep. 17, 1996

[54] BENZODIAZEPINE DERIVATIVES

[75] Inventors: Mark S. Chambers, Watford; Stephen R. Fletcher, Nr. Bishops Stortford, both of England

[73] Assignee: Merck Sharp & Dohme Ltd., Hoddesdon, England

[21] Appl. No.: 496,840

[22] Filed: Jun. 29, 1995

Related U.S. Application Data

[63] Continuation of Ser. No. 350,759, Dec. 7, 1994, abandoned.
[51] Int. Cl.$^6$ .................. C07D 243/24; C07D 413/12; C07D 403/12; A61K 31/55
[52] U.S. Cl. ................................................. 540/509
[58] Field of Search .......................... 540/509; 514/221

[56] References Cited

U.S. PATENT DOCUMENTS

| | | | |
|---|---|---|---|
| 4,820,834 | 4/1989 | Evans et al. | 540/504 |
| 5,010,076 | 4/1991 | Waldeck et al. | 514/221 |
| 5,218,114 | 6/1993 | Bock | 540/509 |
| 5,360,802 | 11/1994 | Chambers | 540/509 |

FOREIGN PATENT DOCUMENTS

| | | | |
|---|---|---|---|
| 0167919A2 | 1/1986 | European Pat. Off. . | |
| 0284256A1 | 9/1988 | European Pat. Off. . | |
| 0387618A1 | 9/1990 | European Pat. Off. . | |
| 93/02078 | 2/1993 | WIPO . | |
| 93/16999 | 9/1993 | WIPO | 540/509 |

OTHER PUBLICATIONS

Koszykcki, Clin. Neuropharm. 15, Suppl 1, PtB p. 598 (1992).
V. Mutt, "Gastrointestinal Hormones," G. B. J. Green, Ed., Raven Press, NY, pp. 169–221 and G. Nission, ibid pp. 127–167.
Mutt and Jorpes, Biochem. J., 125, 678 (1981).
A. J. Stunkard and E. Stellar, Ed., "Eating and Its Disorders" Raven Press, New York, 1984, p. 67.
A. J. Prange, et al., "Peptides in the Central Nervous System", Ann Repts. Med. Chem. 17, 31, 33 (1982).
J. A. Williams, Biomed, Res. 3 107 (1982).
J. E. Morley, Life, Sci. 30, 479 (1982).
T. H. Moran, et al. "Two Brain cholecystokinin receptors: implications for behavoural actions", *Brain Res.*, pp. 175–179 (1986).
P. L. Faris, et al, Science, 226, 1215 (1984).
M. F. O'Neill, et al., Brain Research, 534 287 (1990).
Rasmusson, et al., 1991, Eur. J. Pharmacol., 209, 135–138.
Woodruff, et al., 1991, Neuropeptides 19, 45–46.
Cervo, et al., 1988, Eur. J. Pharmacol., 158, 53–59.
Singh, et al., 1992, Br. J. Pharmacol., 105, 8–10.
K. Okyama, Hokkaido J. Med. Sci., 206–216 (1985).
Xue, et al., Peptides, 8, 1987, 769–772.
Almegand Eur. J. Pharmacol., 211 (2) 183–187 (1992).
A. Bill, et al., Acta Physiol. Scand., 138 479–485 (1990).

M. Bock, et al., J. Med. Chem., 32, 13–16 (1989).
Coppa, et al., Ann. Surg., 202–203 (1985).
"Chapter 4. Peptides in the Central Nervous System: Focus on Thyrotropin Releasing Hormone and Neurotensin", A. J. Prange, Jr. and C. B. Nemeroff, Annual Reports in Medicinal Chemistry, (1982), vol. 17, pp. 31, 33.
"Cholecystokinin: A Hormone and a Neurotransmitter", J. A. Williams, Biomedical Research (1982), vol. 3, pp. 107–121.
"Minireview—The Ascent of Cholecystokinin (CCK)— from Gut to Brain", J. E. Morley, Life Sciences, (1982), vol. 30, No. 6, pp. 479–493.
"Two brain cholecystokinin receptors: implications for behavioral actions", T. H. Moran, et al., Brain Research, (1986), vol. 362, pp. 175–179.
"Morphine Analgesia Potentiated but Tolerance Not Affected by Active Immunization Against Cholecystokinin", P. L. Faris, et al., Science, (Dec. 1984), vol. 226, pp. 1215–1217.
"Blockade of CCK–B receptors by L–365, 260 induces analgesia in the squirrel monkey", M. F. O'Neill, et al., Brain Research, (1990), vol. 534, pp. 287–290.
"Cholecystokinin (CCK) and schizophrenia: the selective CCKBETA antagonist LY262691 decreases midbrain dopamine unit activity", K. Rasmussen, et al., European Journal of Pharmacology, (1991), vol. 209, pp. 135–138.
"Functional Role of Brain CCK Receptors", G. N. Woodruff, et al., Neuropeptides, (1991), vol. 19, (Suppl.) pp. 45–46.
"8–Hydroxy-2-(di-n-propylamino)tetralin, a selective serotonin 1A receptor agonist, reduces the immobility of rats in the forced swimming test by acting on the nucleus raphe dorsalis", L. Cervo, et al., European Journal of Pharmacology, (1988), vol. 158, pp. 53–59.
"The antagonism of benzodiazepine withdrawal effects by the selective cholecystokininBeta receptor antagonist CI–988", L. Singh, et al., British Journal of Pharmacology, (1992), vol. 105, pp. 8–10.

(List continued on next page.)

*Primary Examiner*—Mark L. Berch
*Attorney, Agent, or Firm*—Robert J. North; Melvin Winokur

[57] ABSTRACT

Compounds of the formula (I):

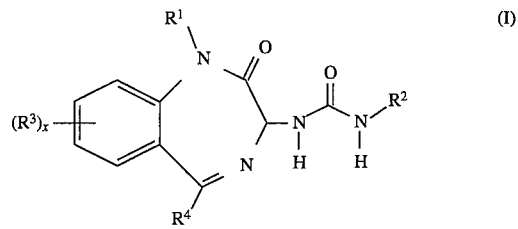

wherein $R_1$ is hydrogen or specified optionally substituted alkyl, $R^2$ is specified optionally substituted phenyl or pyridyl, x is 0, 1, 2 or 3, $R^3$ is a specified alkyl, halo or amino and $R^4$ is specified cycoalkyl or bicycloalkyl; and salts and prodrugs thereof, are useful as antagonists of cholecystokin and gastrin receptors.

7 Claims, No Drawings

OTHER PUBLICATIONS

"Effects of the Anti-Tumor Drugs and Gastrointestinal Hormones on the Growth of the Pancreatic Duct Cell Adenocarcinoma in the Homologous Transplanted Animal Models", K. Okyama, Hokkaido Journal of Medical Science, (1985), pp. 206–216.

"The Influence of Proglumide, a Putative CCK Antagonist, on Cerebral Ischemia in Gerbil", C. Xue, et al., Peptides, (1987), vol. 8, pp. 769–772.

"Cholecystokinin contracts isolated human and monkey iris sphincters; a study with CCK receptor antagonists", B. Almegard, et al., European Journal of Pharmacology, (1992), vol. 211, pp. 183–187.

"Chapter 7 Cholecystokinin: Isolation, Structure, and Functions", Vildor Mutt, Gastrointestinal Hormones, Raven Press, NY, 1980, pp. 169–221;"Chapter 6 Gastrin: Isolation, Characterization, and Functions", Goran Nisson, Gastrointestinal Hormones, Raven Press, NY, 1980, pp. 127–167.

"Hormonal Polypeptides of the Upper Intestine", V. Mutt and E. Jorpes, Journal of Biochemistry, (1981), vol. 125, p. 678.

"Gut Hormone Hypothesis of Postprandial Satiety", G. P. Smith, edited by A. J. Stunkard and E. Stellar, Raven Press, NY (1984) pp. 67–75.

Regulatory Peptides, 35 (1991), pp. 1–10, by S. Kawa bata et al. "The Effect of cholecytstokinin receptor antagonists MK–329 and L–365, 260 . . . "Am. Soc. Pharm. Ex. Ther., 46:943–948. 1994, by S. Patel et al. "Biological Properties of the Benzodiazepine Amidine Derivative L–740, 093 . . . ".

"Cholecystokinin causes contraction of the pupilary sphincter in monkeys but not in cats, rabbits, rats, and guinea-pigs: antagonism by lorglumide", A. Bill, et al., Acta Physiol. Scand., (1990), vol. 138, pp. 479–485.

"Benzodiazepine Gastrin and Brain Cholecystokinin Receptor Ligands: L–365, 260", M. G. Bock, et al., Journal of Medicinal Chemistry, (1989), vol. 32, pp. 13–16.

"Hepatic Resection for Metastatic Colon and Rectal Cancer—An Evaluation of Preoperative and Postoperative Factors", G. F. Coppa, et al., Annual Surgery, (Aug. 1985), vol. 202, pp. 203–208.

"L–365,260, a CCKBeta Antagonist, Blocks CCK–4–Panic in Panic Disorder", D. Koszycki, Clinical Neuropharmacology, (1992), vol. 15, Suppl. 1, Part B, 59B.

Kawabata, *Regulatory Peptides* 35, pp. 1–10 (1991).

Patel, Molecular Pharm 46, 943 (1994).

BENZODIAZEPINE DERIVATIVES

This is a continuation of application Ser. No. 08/350,759, filed Dec. 7, 1994, abandoned.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, New York, p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-NH$_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed-CCK-A and CCK-B (T. H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

The present invention provides benzodiazepine compounds of formula (I):

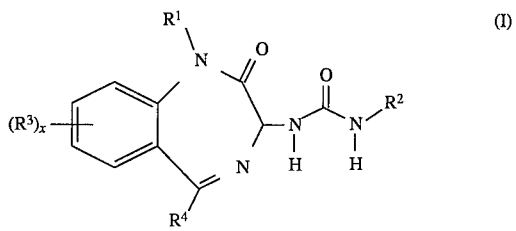

wherein:

R$^1$ represents H, C$_{1-6}$alkyl, C$_{3-7}$cycloalkyl, cyclopropylmethyl, CH$_2$CO$_2$R$^5$ (where R$^5$ is C$_{1-4}$alkyl), CH$_2$CONR$^6$R$^7$ (where R$^6$ and R$^7$ each independently represents H or C$_{1-4}$alkyl, or R$^6$ and R$^7$ together form a chain (CH$_2$)$_p$ where p is 4 or 5), C$_{1-6}$alkylNR$^8$R$^9$ or C$_{1-6}$alkylCONR$^8$R$^9$ where R$^8$ and R$^9$ together with the nitrogen atom to which they are attached form a 5 to 8 membered non-aromatic ring system containing a second heteroatom selected from O, S or NR$^{10}$, where R$^{12}$ is H or C$_{1-4}$alkyl;

R$^2$ represents a phenyl or pyridyl group optionally substituted by one or more substituents selected from C$_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl (where q is 0, 1, 2 or 3), 5-hydroxy-4-pyrone, $NR^6R^7$, $NR^{10}COR^5$, $NR^{10}CONR^{10'}R^5$ (where $R^{10}$ and $R^{10'}$ are each independently H or $C_{1-4}$alkyl and $R^5$ is as previously defined), $CONR^6R^7$ (where $R^6$ and $R^7$ are as previously defined), $SO(C_{1-6}alkyl)$, $SO_2(C_{1-6}alkyl)$, trifluoromethyl, $CONHSO_2R^{11}$, $SO_2NHCOR^{11}$ (where $R^{11}$ is $C_{1-6}$alkyl, optionally substituted aryl, 2,2-difluorocyclopropane or trifluoromethyl), $SO_2NHR^{12}$ (where $R^{12}$ is a nitrogen containing heterocycle), $B(OH)_2$ or $(CH_2)_qCO_2H$, where q is as previously defined; or $R^2$ represents a group

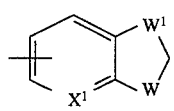

where $X^1$ represents CH or N; W represents $CH_2$ or $NR^{10}$, where $R^{10}$ is as previously defined, and $W^1$ represents $CH_2$, or W and $W^1$ each represent O; or $R^2$ represents phenyl substituted by a group

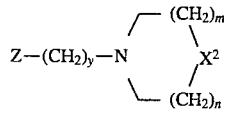

wherein $X^2$ is O, S or $NR^{10}$, where $R^{10}$ is as previously defined; Z is a bond, O or S; m is 1, 2 or 3; n is 1, 2 or 3; and y is 0, 1, 2 or 3;

Each $R^3$ represents $C_{1-6}$alkyl, halo or $NR^6R^7$, where $R^6$ and $R^7$ are as previously defined;

$R^4$ represents bridged $C_{6-10}$bicycloalkyl or $C_{3-7}$cycloalkyl optionally substituted by one or more $C_{1-4}$alkyl groups;

x is 0, 1, 2 or 3;

with the proviso that when $R^1$ is H, $C_{1-6}$alkyl, $C_{3-7}$cycloalkyl, cyclopropylmethyl, $CH_2CO_2R^5$ or $CH_2CONR^6R^7$, $R^2$ represents phenyl substituted by

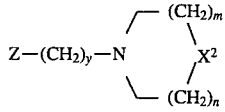

and salts and prodrugs thereof.

It will be appreciated that formula (I) is intended to embrace all possible isomers, including optical isomers, and mixtures thereof, including racemates.

As used herein, the definition of each expression, when it occurs more than once in any structure, is intended to be independent of its definition elsewhere in the same structure.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

Halo includes fluoro, chloro, bromo and iodo. Preferably halo will be fluoro or chloro.

As used herein, unless otherwise indicated, alkyl means straight or branched chain saturated hydrocarbon.

Unless otherwise stated, aryl means optionally substituted carbocyclic or heterocyclic aromatic groups, especially phenyl.

Heteroaryl means aromatic rings preferably having 5 or 6 ring atoms and containing at least one atom selected from O, S and N.

A first subgroup of compounds according to the invention is represented by compounds of formula (I), and salts and prodrugs thereof, wherein $R^1$ represents $C_{1-6}$alkyl, $C_{3-7}$cycloalkyl, cyclopropylmethyl, $CH_2CO_2R^5$ or $CH_2CONR^6R^7$ (where $R^5$, $R^6$ and $R^7$ are as previously defined);

$R^2$ represents phenyl substituted by a group:

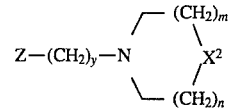

wherein $X^2$, Z, m, n and y are as previously defined; and $R^4$ represents $C_{3-7}$cycloalkyl.

A second subgroup of compounds according to the invention is represented by compounds of formula (I), and salts and prodrugs thereof, wherein $R^1$ represents $C_{1-6}$alkylNR$^8$R$^9$ or $C_{1-6}$alkylCONR$^8$R$^9$; $R^2$ represents a phenyl group optionally substituted by one or more of $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $CONR^6R^7$, $NR^{10}COR^{11}$, $NR^{10}CONR^{10'}R^5$, $SO(C_{1-6}alkyl)$, $SO_2(C_{1-6}alkyl)$, trifluoromethyl, $CONHSO_2R^{11}$, $SO_2NHCOR^{11}$, $SO_2NHCOR^{11}$, $SO_2NHR^{12}$, $B(OH)_2$, $(CH_2)_qCO_2H$; or $R^2$ represents a group

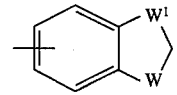

where W and W' are as previously defined.

In one preferred subgrup of compounds according to the invention, $R^1$ represents $C_{1-6}$alkyl, such as $C_{1-4}$alkyl, for example, methyl, ethyl, n-propyl or i-butyl.

In another preferred subgroup of compounds of the invention, $R^1$ represents $C_{2-3}$alkylNR$^8$R$^9$, where the group NR$^8$R$^9$ preferably represents morpholinyl.

Suitable values for $R^{11}$ include methyl, ethyl, i-propyl, t-butyl, phenyl and trifluoromethyl.

When $R^{11}$ is optionally substituted aryl, this will preferably be optionally substituted phenyl. Suitable substituents include $C_{1-4}$alkyl, $C_{1-4}$alkoxy, halo and trifluoromethyl. Preferred is unsubstituted phenyl or phenyl substituted by $C_{1-6}$alkyl, for example, phenyl substituted by $C_{1-6}$alkyl in the ortho position.

When $R^{11}$ is $C_{1-6}$alkyl, it will preferably represent $C_{1-4}$alkyl. Particularly preferred are methyl and iso-propyl, especially iso-propyl.

When $R^2$ is phenyl or pyridyl substituted by $SO_2NHR^{12}$, suitable values of $R^{12}$ include, for example, thiazole, thiadiazole and pyrazine.

Preferably q is zero.

When $R^2$ represents optionally substituted phenyl or pyridyl, the substituents will preferably be selected from $C_{1-6}$alkyl, such as methyl and ethyl, halo, such as chloro, bromo, fluoro and iodo, and trifluoromethyl.

When $R^2$ represents monosubstituted phenyl, the substituent will preferably be located at the 3- or 4-position of the phenyl ring, more preferably at the 3-position. When $R^2$ represents disubstituted phenyl the substituents will preferably be located at the 3- and 4-positions of the phenyl ring.

When $R^2$ represents optionally substituted pyridyl it will preferably represent optionally substituted 3-pyridyl. When $R^2$ represents monosubstituted 3-pyridyl, the substituent will preferably be located at the 5-position of the pyridyl ring.

When $R^2$ represents a group

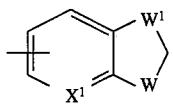

where $X^1$ is CH the fused 5-membered ring will preferably be fused across the 3- and 4-positions of the phenyl ring and where $X^1$ is N the 5-membered ring will preferably be fused across the 4- and 5-positions of the pyridyl ring.

Preferably W and $W^1$ are $CH_2$.

When $R^2$ represents phenyl substituted by a group

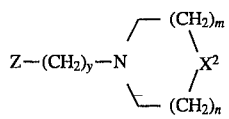

the substituent will preferably be located at the 3- or 4-position of the phenyl ring, more preferably at the 3-positions.

Preferably m is 1 or 2, more preferably 1.

Preferably n is 1 or 2, more preferably 1.

Preferably y is 0 or 1, more preferably 0.

Suitable values for $X^2$ include O, S, NH and $NCH_3$.

Preferably Z represents a bond.

Suitable values for $R^3$ include methyl and dimethylamino.

Preferably x is 0 or 1, more preferably 0.

When $R^4$ represents $C_{6-10}$bicycloalkyl, it will preferably contain 7, 8 or 9 carbon atoms, more preferably 7 carbon atoms. A suitable example of a $C_{6-10}$bicycloalkyl substituent is:

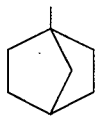

When $R^4$ represents $C_{3-7}$cycloalkyl optionally substituted by one or more $C_{1-4}$alkyl groups, it will preferably represent optionally substituted cyclobutyl, cyclopentyl, cyclohexyl or cycloheptyl, more preferably cyclohexyl or cycloheptyl optionally substituted by one or more $C_{1-4}$alkyl groups. Preferably $C_{1-4}$alkyl represents methyl.

Preferred are compounds wherein the $C_{3-7}$cycloalkyl group is unsubstituted.

A preferred subgroup of compounds according to the invention is represented by compounds of formula (Ia):

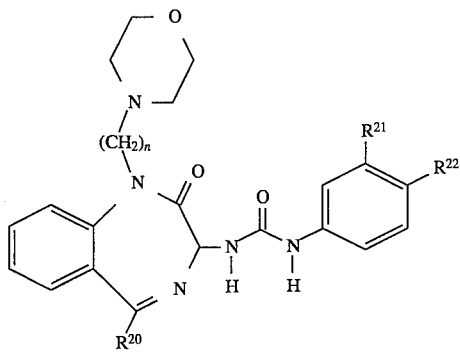

(Ia)

wherein $R^{20}$ is $C_{4-7}$cycloalkyl;

$R^{21}$ is $C_{1-4}$alkyl, preferably methyl, and $R^{22}$ is H, or $R^{21}$ and $R^{22}$ together form a chain $(CH_2)_3$;

n is 2 or 3;

and salts and prodrugs thereof.

A further preferred subgroup of compounds according to the invention is represented by compounds of formula (Ib):

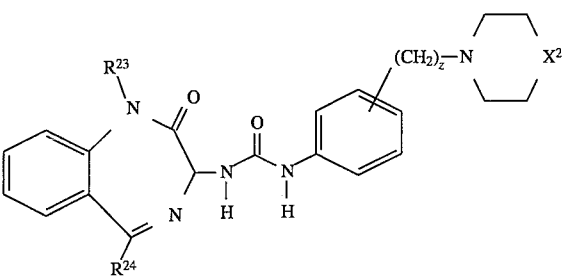

(Ib)

wherein $X^2$ is as defined for formula (I);

$R^{23}$ is $C_{1-6}$alkyl, preferably $C_{1-4}$alkyl;

$R^{24}$ is cyclopentyl, cyclohexyl or cycloheptyl; more preferably cyclohexyl or cycloheptyl;

z is 0 or 1;

and salts and prodrugs thereof.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic salts. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical compostion, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss, or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage wll be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

According to one general process (A), the compounds of formula (I) may be prepared by reaction of intermediates of formula (II) with compounds of formula (III)

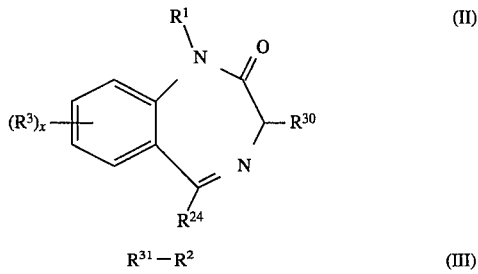

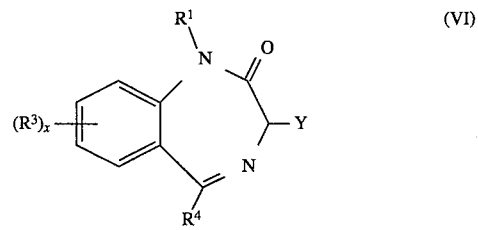

wherein $R^1$, $R^2$, $R^3$, $R^4$ and x are as defined for formula (I) above, one of $R^{30}$ and $R^{31}$ represents $NH_2$ and the other of $R^{30}$ and $R^{31}$ represents —N═C═O.

The reaction is conveniently effected in a suitable organic solvent, such as an ether, for example, tetrahydrofuran.

According to a second general process, (B), compounds of formula (I) may be prepared by reacting a compound of formula (VI)

wherein $R^1$, $R^3$, $R^4$ and x are defined for formula (I) and Y represents an activated carbamate, with an amine of formula (III) wherein $R^{31}$ is $NH_2$ (hereinafter intermediates (IIIA)), in the presence of a base.

An "activated carbamate" is a carbamate group which bears a substituent which activates the carbamate function to nucleophilic attack. Suitably Y may represent an appropriately substituted aryl carbamate of formula

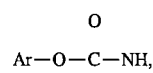

for example

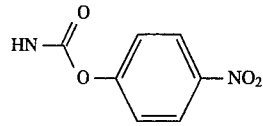

Suitable bases for use in the reaction include tertiary amines, for example, triethylamine.

The reaction is conveniently effected in a suitable organic solvent, for example, dimethylformamide, at ambient or elevated temperature. Preferably the reaction is conducted at approximately 50° C.

Intermediates of formula (II) wherein $R^{30}$ is $NH_2$ (hereinafter intermediates (IIA)) may be prepared from compounds of formula (VIII)

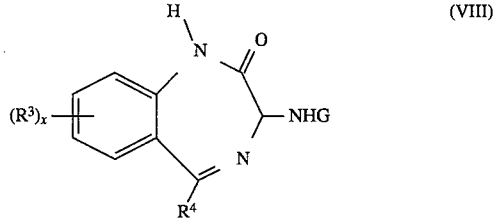

wherein $R^3$, $R^4$ and x are as defined for formula (I) and G is a protecting group; by reaction with a reagent suitable to introduce the group $R^1$, for example a halide of formula $R^1$Hal where Hal represents halo such as chloro, bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene, followed by deprotection.

Compounds of formula (VIII) may be prepared from compounds of formula (IX)

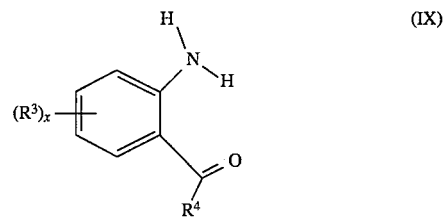

wherein $R^3$, $R^4$ and x are as defined for formula (I) by a reaction sequence comprising:

(i) reaction with a compound of formula (X)

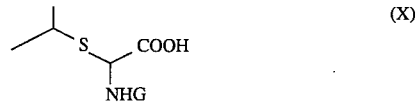

wherein G is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) isobutyl chloroformate or, preferably, bis(2-oxo-3-oxazolidinyl)phosphonic chloride (BOP-Cl).

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran.

(iii) Treatment with an organic acid, for example acetic or propionic acid, optionally in the presence of an ammonium salt, for example ammonium acetate.

Compounds of formula (IX) may be prepared by reaction of a compound of formula (XI) with a compound of formula (XII)

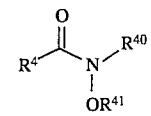 (XI)

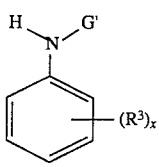 (XII)

wherein $R^3$, $R^4$ and x are as defined for formula (I), $R^{40}$ and $R^{41}$ each represent $C_{1-4}$alkyl, preferably methyl, and G' represents a protecting group, such as t-butoxycarbonyl group, in the presence of a base, followed by deprotection.

Suitable bases of use in the reaction include organolithiums, such as butyllithiums, for example t-butyllithium.

The reaction is conveniently effected in a suitable organic solvent, such as an ether, for example tetrahydrofuran, at low temperature.

Compounds of formula (XI) may be prepared from the corresponding acids of formula $R^4COOH$, wherein $R^4$ is as defined for formula (I), by reaction with an amine of formula $R^4ONHR^{40}$, wherein $R^{40}$ and $R^{41}$ are as previously defined, in the presence of a base and a coupling agent.

Suitable bases of use in the reaction include tertiary amines such as, for example, triethylamine. The reaction is conveniently effected in a suitable organic solvent, such as dimethylformamide. A preferred coupling agent of use in the reaction is 1-(3-dimethylaminopropyl)-3-ethylcarbodiimide hydrochloride (EDC).

Compounds of formula (XII) and acids of formula $R^4COOH$ are commercial available or may be prepared from commercially available starting materials by conventional methods well known to those skilled in the art.

Alternatively, compounds of formula (IX) may be prepared by reaction of a compound of formula (XIV)

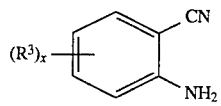 (XIV)

wherein $R^3$ and x are previously defined, with a Grignard reagent of formula $R^4MgHal$ wherein $R^4$ is cycloalkyl and Hal is halo such as chloro, bromo or iodo.

Compounds of formula (XIV) are commercially available or may be prepared from commercially available compounds by conventional methods.

Intermediates of formula (II) wherein $R^{30}$ is —N=C=O (IIB) may be prepared from amines of formula (II) wherein $R^{30}$ is $NH_2$ (IIA) by reaction with triphosgene in the presence of a base, such as a tertiary amine, for example, triethylamine. The reaction is conveniently effected in a suitable organic solvent, such as an ether, for example, tetrahydrofuran, suitably at low temperature, such as about 0° C.

Intermediates of formula (VI) may be prepared from compounds of formula (IIA) by reaction with a suitable haloformate of formula

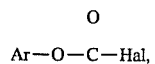

where Hal is as previously defined, preferably chloro, for example

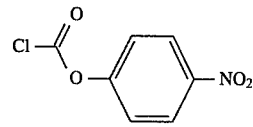

in the presence of a base, such as a tertiary amine, for example, triethylamine.

Isocyanates of formula (III) wherein $R^{31}$ is —N=C=O (IIIB) may be prepared from amines of formula (IIIA) by conventional methods.

Amines of formula (IIIA) are known compounds, or may be prepared from the corresponding nitro compounds of formula $R^2NO_2$, wherein $R^2$ is as previously defined, by reduction.

Suitably the reduction is effected by catalytic hydrogenation, for example, using a noble metal catalyst such as palladium which may be supported, e.g. on carbon. The reaction is conveniently effected in a suitable organic solvent, such as an alcohol, e.g. ethanol.

Compounds of formula (XVI) are commercially available or may be prepared by the procedures described in the accompanying Examples or by alternative procedures which will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof. 4B, 5 and 6 of International Patent Application PCT/GB92/01366 published as WO 93/02078. When tested for CCK Receptor Binding, Pancreas and Brain, by the method described in PCT/GB92/01366 (WO 93/02078) the compounds of the Examples displayed an $IC_{50}<1$ mM at the CCK receptor.

EXAMPLE 1

N-[3(R,S)-5-Cycloheptyl-2,3-dihydro-1-(2-(N-morpholino)ethyl)-2-oxo-1H-1,4-benzodiazepin-3-yl] N'-[3-methylphenyl] urea Step 1: 2-Aminophenylcycloheptylmethanone Over a period of 1 h a solution of cycloheptyl bromide (37.8 g) in diethyl ether (200 ml) was added dropwise to a slurry of magnesium turnings (5.28 g) and a crystal of iodine in diethyl ether (20 ml) at reflux. The mixture was stirred for a further hour whereupon the Grignard solution was cannulated into a pressure equalising dropping funnel, attached to a three-necked round-bottomed flask, which was under an atmosphere of nitrogen.

A solution of 2-aminobenzonitrile (8.26 g) in diethyl ether (200 ml), at 0° C., was treated dropwise with the Grignard reagent prepared above, over a period of 30 min. Once the addition was complete, the mixture was warmed to room temperature and stirred for 16 h under nitrogen. The solution was cooled to 0° C., quenched with 5N hydrochloric acid (45 ml), and basified using solid sodium hydroxide (8.9 g). The aqueous solution was extracted with ethyl acetate (2×100 ml) and the combined organic layers were dried ($Na_2SO_4$) and evaporated. The residue was chromatographed on silica gel using 2:1 petrol:ethyl acetate as the eluant. This gave the title compound (8.2 g) as a pale yellow oil. $^1$H NMR (250 MHz, $CDCl_3$) δ 1.40–2.10 (12H, m), 3.34–3.50 (1H, m), 6.30 (2H, brs), 6.60–6.70 (2H, m), 7.20–7.30 (1H, m), 7.70–7.80 (1H, m). TLC (silica, petrol (60/80):ethyl acetate 2:1). Rf= 0.50.

Step 2: Cycloheptyl-2-(α-(benzyloxycarbonylamino)-α-iso-propylthioacetylamino)phenyl methanone α-(iso-Propylthio)-N-(benzyloxycarbonyl)glycine (21.9 g) was dissolved in dichloromethane (450 ml) and cooled to 0° C. The stirred solution was then treated with triethylamine (21.5 ml), bis(2-oxo-3-oxazolidinyl)phosphinic chloride (19.7 g) and 2-aminophenyl cycloheptyl methanone (12.0 g). The mixture was warmed to ambient temperature and stirred for 2 h. The mixture was then washed in succession with 10% citric acid solution (100 ml), water (100 ml), saturated sodium bicarbonate solution (100 ml) and brine (100 ml). The dried ($Na_2SO_4$) organic phase was evaporated and the residue chromatographed on silica gel using 8:1 petrol:ethyl acetate as eluant. This afforded the title compound as a colourless solid (13.5 g). $^1$H NMR (250 MHz, $CDCl_3$) δ 1.10–2.00 (18, m), 3.14–3.34 (1H, m), 3.40–3.56 (1H, m), 5.16–5.22 (2H, m), 5.56 (1H, d, J=5 Hz), 5.98 (1H, d, J=5 Hz), 7.10–7.18 (1H, m), 7.24–7.44 (5H, m), 7.50–7.60 (1H, m), 7.84–7.94 (1H, m), 8.60–8.70 (1H, m), 12.28 (1H, brs). TLC (silica, petrol (60/80):ethyl acetate 3:1). Rf= 0.45.

Step 3: 3(R,S)-[(Benzyloxycarbonyl)amino]-5-cycloheptyl- 1,3-dihydro-2H -1,4-benzodiazepin-2-one Cycloheptyl-2-(α-(benzyloxycarbonylamino)-α-iso-propylthioacetylamino)phenyl methanone (10 g) was dissolved in anhydrous tetrahydrofuran (500 ml) and cooled to 0° C. Ammonia gas was bubbled through the stirred solution for 10 min before adding mercuric chloride (8.5 g) in one portion. Ammonia was continually bubbled through the solution for a further hour, then the suspended solids were filtered off. The solvent was evaporated in vacuo to leave an oil, which was used without further purification.

The crude α-aminoglycinamide was dissolved in glacial acetic acid (200 ml) and treated with ammonium acetate (7.7 g). The resulting reaction mixture was stirred at room temperature overnight, before removing the solvent in vacuo. The residue was partitioned between ethyl acetate (300 ml) and 10% sodium hydroxide solution (200 ml). The dried ($Na_2SO_4$) organic layer was evaporated and the residue chromatographed on silica gel with 2:1 petrol:ethyl acetate as eluant. This afforded the title product (8.0 g) as a colourless solid. $^1$H NMR (250 MHz, $CDCl_3$) δ 1.18–2.20 (12H, m), 2.90–3.07 (1H, m), 5.06–5.24 (3H, m), 6.46 (1H, d, J=10 Hz), 7.04–7.12 (1H, m), 7.22–7.42 (6H, m), 7.44–7.56 (1H, m), 7.58–7.68 (1H, m), 10.30 (1H, brs). TLC (silica, petrol (60/80):ethyl acetate 2:1). Rf= 0.15.

Step 4: 3(R,S)-[(Benzyloxycarbonyl)amino]-5-cycloheptyl- 1,3-dihydro-1-(2-(N-morpholino)ethyl)-2H-1,4-benzodiazepin-2-one 3(R,S)-[(Benzyloxycarbonyl)amino]-5-cycloheptyl-1,3-dihydro-2H-1,4-benzodiazepin-2-one (0.5 g) in anhydrous dimethylformamide (20 ml) was treated with cesium carbonate (1.2 g) and N-(2 -chloroethyl)morpholine (0.6 g). The mixture was stirred at 60° C. for 16 h. The undissolved material was removed by nitration. The solvent was evaporated and the residue partitioned between ethyl acetate (50 ml) and water (30 ml). The organic phase was separated, dried ($Na_2SO_4$) and evaporated in vacuo. The residue was triturated with diethyl ether to afford the title compound (0.43 g) as a colourless solid, mp 130°–2° C. $^1$H NMR (250 MHz, $D_6$-DMSO) δ 1.14–1.86 (11H, m), 1.92–2.08 (1H, m), 2.10–2.38 (6H, m), 3.04–3.20 (1H, m), 3.36–3.54 (4H, m), 3.76–3.92 (1H, m), 4.24–4.40 (1H, m), 4.88 (1H, d, J=8.3 Hz), 5.00, 2H, s), 7.14–7.40 (5H, s), 7.54–7.80 (3H, m), 8.20 (1H, d, J=8.3 Hz).

Step 5: 3(R,S)-Amino-5-cycloheptyl-1,3-dihydro-1-(2 -(N-morpholino)ethyl)-2H-1,4-benzodiazepin-2-one 3(R,S)-[(Benzyloxycarbonyl)amino]-5-cycloheptyl-1,3-dihydro-1-( 2-(N-morpholino)ethyl)-2H-1,4-benzodiazepin-2-one (300 mg) was treated with a solution of 30% hydrogen bromide in glacial acetic acid (15 ml) and stirred for 20 min at room temperature. The mixture was then added dropwise onto cold (0° C.) diethyl ether (50 ml). A colourless solid precipitated which was filtered off. The solid was treated with 10% sodium hydroxide solution (50 ml) then extracted with ethyl acetate (80 ml). The organic layer was separated, dried ($Na_2SO_4$) and evaporated to afford the title compound (218 mg) as a colourless oil. TLC (silica/dichloromethane:methanol 9:1) Rf, 0.40. $^1$H NMR (250 MHz, $CDCl_3$) δ: 1.26–1.74 (9H, m), 1.76–1.96 (2H, m), 2.00–2.16 (1H, m), 2.30–2.60 (8H, m), 2.88–3.00 (1H, m), 3.50–3.70 (4H, m), 3.72–3.86 (1H, m), 4.30–4.42 (1H, m), 7.20–7.30 (1H, m), 7.40–7.60 (3H, m).

Step 6: N-[3(R,S)-5-Cycloheptyl-2,3-dihydro-1-(2 -(N-morpholino)ethyl)-2-oxo-1H-1,4-benzodiazepin-3-1]N'-3 -methylphenyl]urea 3(R,S)-Amino-5-cycloheptyl-1,3-dihydro-1-(2 -(N-morpholino)ethyl)-2H-1,4-benzodiazepin-2-one (214 mg) in dry tetrahydrofuran (5 ml) was treated with 3-methylphenyl isocyanate (72 μl). The mixture was stirred for 30 min. The solvent was evaporated and the residue triturated with diethyl ether to afford the title compound (100 mg) as a colourless solid, mp 206°–207° C. $^1$H NMR (360 MHz, $D_6$-DMSO) δ 1.14–1.80 (11H, m), 1.95–2.06 (1H, m), 2.10–2.37 (9H, m), 3.08–3.19 (1H, m), 3.36–3.50 (4H, m), 3.80–3.93 (1H, m), 4.25–4.35 (1H, m), 5.00 (1H, d, J=8.4 Hz), 6.71 (1H, d, J=6.6 Hz), 7.04–7.14 (2H, m), 7.17 (1H, s), 7.25 (1H, d, J=8.5 Hz), 7.37 (1H, t, J=7.1 Hz), 7.61 (1H, t, J=8.5 Hz), 7.67–7.82 (2H, m), 8.86 (1H, s).

EXAMPLE 2

N-[3(R,S)-5-Cylohexyl-2,3-dihydro-1-(2-(N-morpholino)ethyl)-2-oxo-1H-1,4-benzodiazepin-3-yl]-N'-[3-methylphenyl] urea Step 1: (2-Acetamidophenyl) cyclohexyl methanone Cyclohexylmagnesium bromide (240 ml of a 2M solution in ether) in ether (200 ml) was added dropwise to a solution of 2-methyl-4H-3,1-benzoxazin-4-one (100 g) in ether (1100 ml) at −10° C. over 2 h. The mixture was stirred at this temperature for 2 h, then at ambient temperature for 30 min. After cooling to −10° C. the suspension was treated with 2M HCl (600 ml), keeping the temperature below 0° C. After stirring for 15 min the layers were separated, and the ethereal layer washed sequentially with water (500 ml), 5% sodium hydroxide solution (2×500 ml) and finally water (2×500 ml). The organic layer was separated, dried (MgSO$_4$), evaporated in vacuo and chromatographed on silica gel using petrol:ethyl acetate (2:1) to give (2-acetamidophenyl) cyclohexyl methanone (28 g). Mp 66° C. $^1$H NMR (CDCl$_3$, 360 MHz) δ 1.25–1.89 (10H, m), 2.23 (3H, s), 3.33 (1H, m), 7.13 (1H, d of t, J=6 and 1 Hz), 7.53 (1H, d of t, J=6 and 1 Hz), 7.92 (1H, d, J=6 Hz), 8.76 (1H, d, J=6 Hz), 11.73 (1H, brs).

Step 2: (2-Aminophenyl) cyclohexyl methanone

A solution of (2-acetamidophenyl) cyclohexyl methanone (0.53 g) in methanol (5 ml) and concentrated hydrochloric acid (15 ml) was heated at 80° C. for 1 h. After this time the solution was cooled to ambient temperature and the solvents removed in vacuo. The residue was dissolved in water (10 ml) and basified with 4N sodium hydroxide solution (20 ml). The mixture was then extracted into ethyl acetate (4×20 ml) and the organic layers combined and dried (MgSO$_4$). The solvent was evaporated and the residue chromatographed on silica gel using petrol:ethyl acetate (2:1), to afford the amine (0.40 g). Mp 73°–75° C. $^1$H NMR (360 MHz, CDCl$_3$) δ 1.23–2.09 (10H, m), 3.27 (1H, m), 6.29 (2H, brs), 6.64 (2H, m), 7.25 (1H, dt, J=6 and 1 Hz), 7.76 (1H, dd, J=7 and 1 Hz).

Step 3: 3(R,S)-[(Benzyloxycarbonyl)amino]-5-cyclohexyl-1,3-dihydro-2H-1,4-benzodiazepin-2-one α-(Isopropylthio)-N-(benzyloxycarbonyl)glycine (30 g) was dissolved in dichloromethane (1000 ml) and cooled to 0° C. The stirred solution was then treated with N-methyl morpholine (11.5 ml) followed by isobutyl chloroformate (13.7 ml). The resulting reaction mixture was stirred for a further 15 min at 0° C., then heated to reflux. The refluxing reaction mixture was treated dropwise, over 20 min, with a solution of (2-aminophenyl) cyclohexyl methanone (20.5 g) in dichloromethane (140 ml). After addition was complete the reaction was heated at reflux for a further 4 h. The mixture was then washed in succession with 10% citric acid solution (2×500 ml), saturated sodium bicarbonate solution (2×500 ml) and brine (500 ml). The dried (MgSO$_4$) organic phase was evaporated to afford the crude product as a pale orange solid, which was used without further purification.

The crude (isopropylthio)glycinamide was dissolved in anhydrous tetrahydrofuran (800 ml) and cooled to 0° C. Ammonia gas was bubbled through the stirred solution for 30 min before adding mercuric chloride (33 g) in one portion. Ammonia was continually bubbled through the solution for a further 5 hours, then the suspended solids were filtered off. The solvent was evaporated in vacuo.

The crude α-aminoglycinamide was dissolved in glacial acetic acid (500 ml) and treated with ammonium acetate (36.2 g). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO$_4$) and evaporated. The residue was chromatographed on silica gel, using 2:1 petrol:ethyl acetate as the eluant, to afford 3(R,S)-[(benzyloxycarbonyl)amino]-5-cyclohexyl-1,3-dihydro-2H-1,4-benzodiazepin-2-one (25 g). Mp 164°–166° C. $^1$H NMR (360 MHz, CDCl$_3$) δ 1.07–2.04 (10H, m), 2.77 (1H, m), 5.12 (3H, m), 6.44 (1H, d, J=8 Hz), 7.08 (1H, d, J=8 Hz), 7.23–7.36 (6H, m), 7.46 (1H, t, J=7 Hz), 7.59 (1H, d, J=8 Hz), 8.60 (1H, brs).

Step 4: 3(R,S)-[(Benzyloxycrbonyl)amino]-5-cyclohexyl-1,3-dihydro-1-(N-(2-ethyl)morpholino)-2H-1,4-benzodiazepin-2-one Prepared from 3(R,S)-[(Benzyloxycarbonyl)amino]-5-cyclohexyl-1,3-dihydro-2H-1,4-benzodiazepin-2-one (1.0 g) by the method of Example 1, Step 4. TLC (silica/dichloromethane:methanol 19:1) Rf, 0.27. $^1$H NMR (250 MHz, D$_6$-DMSO) δ: 0.90–1.69 (8H, m), 1.71–1.89 (1H, m), 1.86–2.00 (1H, m), 2.10–2.34 (6H, m), 2.84–3.00 (1H, m), 3.35–3.50 (4H, m), 3.75–3.90 (1H, m), 4.26–4.40 (1H, m), 4.92 (1H, d, J=7.5 Hz), 5.03 (2H, s), 7.22–7.43 (5H, s), 7.54–7.80 (3H, s), 8.22 (1H, d, J=7.5 Hz).

Step 5: 3(R,S)-Amino-5-cyclohexyl-1,3-dihydro-1-(2-(N-morpholino)ethyl)-2H-1,4-benzodiazepin-2-one Prepared from 3(R,S)-[(benzyloxycarbonyl)amino]-5-cyclohexyl-1,3-dihydro-1-(2-(N-morpholino)ethyl)-2H-1,4-benzodiazepin-2-one (0.86 g) by the method of Example 1, Step 5. TLC (silica/dichloromethane:methanol 9:1) Rf, 0.26. $^1$H NMR (250 MHz, D$_6$-DMSO) δ 0.86–1.70 (8H, m), 1.73–1.86 (1H, m), 1.88–2.00 (1H, m), 2.12–2.30 (6H, m), 2.80–2.94 (1H, m), 3.08 (2H, brs), 3.38–3.46 (4H, m), 3.76–3.88(1H, m), 4.22–4.36 (1H, m), 7.12–7.36 (2H, m), 7.52–7.70 (2H, m).

Step 6: N-[3(R,S)-5-Cyclohexyl-2,3-dihydro-1-(2-(N-morpholino)ethyl)-2-oxo-1H-1,4-benzodiazepin-3-yl] N'-[3-methylphenyl] urea Prepared from 3(R,S)-Amino-5-cyclohexyl-1,3-dihydro-1-(2-(N-morpholino)ethyl)-2H-1,4-benzodiazepin-2-one (300 mg) by the method of Example 1, Step 6. Mp 216.5°–218.5° C. $^1$H NMR (360 MHz, D$_6$-DMSO) δ 1.00–1.70 (8H, m), 1.74–1.84 (1H, m), 1.90–2.00 (1H, m), 2.14–2.86 (9H, m), 2.90–3.01 (1H, m), 3.36–3.50 (4H, m), 3.82–3.90 (1H, m), 4.30–4.39 (1H, m), 5.03 (1H, d, J=8.5 Hz), 6.71 (1H, d, J=7.2 Hz), 7.05–7.14 (2H, m), 7.17 (1H, s), 7.26 (1H, d, J=8.5 Hz), 7.37 (1H, t, J=7.4 Hz), 7.61 (1H, t, J=7.2 Hz), 7.65–7.80 (2H, m), 8.87 (1H, s).

EXAMPLE 3

N-[3(R,S)-5-Cyclohexyl-2,3-dihydro-1-(2-(N-morpholino)ethyl)-2-oxo-1H-1,4-benzodiazepin-3-yl]-N'-[5-indanyl] urea 5-Aminoindane (163 mg) in dry tetrahydrofuran (40 ml) was cooled to 0° C. whereupon triphosgene (121 mg) was added. The mixture was stirred at 0° C. for 2 min, then triethylamine (513 μl) was added portionwise until pH8 was attained. The mixture was then stirred for a further 5 min, allowed to warm to 15° C. and then recooled to 0° C. Then a solution of 3(R,S)-amino-5-cyclohexyl-1,3-dihydro-1-(2-(N-morpholino)ethyl)-2H-1,4-benzodiazepin-2-one [Example 2, Step 5] (300 mg) in anhydrous tetrahydrofuran (5 ml) was added dropwise over 5 min. The mixture was stirred at 0° C. for 5 min, allowed to warm to room temperature and then stirred for a further 30 min. The undissolved material was removed by filtration. The solvent was evaporated in vacuo and the residue partitioned between ethyl acetate (50 ml) and water (20 ml). The organic phase was separated, dried ($Na_2SO_4$) and evaporated. The crude solid was chromatographed on silica gel with a gradient elution of 0–3% methanol in dichloromethane to afford the title compound (114 mg), mp 247° C. (dec.). $^1H$ NMR (360 MHz, $D_6$-DMSO) δ 0.90–1.70 (10H, m), 1.75–1.84 (1H, m), 1.90–2.02 (3H, m), 2.15–2.55 (6H, m), 2.70–2,82 (4H, m), 2.95–3.00 (1H, m), 3.40–3.50 (4H, m), 3.80–3.92 (1H, m), 4.30–4.40 (1H, m), 5.03 (1H, d, J=8.5 Hz), 7.02–7.04 (2H, m), 7.20 (1H, d, J=8.5 Hz). 7.24 (1H, s), 7.37 (1H, t, J=7.4 Hz), 7.61 (1H, t, J=7.2 Hz), 7.70–8.02 (2H, m), 8.80 (1H, s).

EXAMPLE 4

N-[3(R,S)5-Cyclohexyl-2,3-dihydro-2-oxo-1-propyl-1H-1,4-benzodiazepin-3-yl] N'-[4-(N-piperazinyl)phenyl]urea, hydrochloride salt Step 1: 3(R,S)-[(Benzyloxycarbonyl)amino]-5-cyclohexyl-1,3 -dihydro-1-propyl-2H-1,4-benzodiazepin-2-one A solution of 3(R,S)-[(benzyloxycarbonyl)amino]-5-cyclohexyl-1,3-dihydro-2H-1,4-benzodiazepin-2-one (Example 2, Step 3, 2 g) in anhydrous dimethylformamide (15 ml), under an atmosphere of nitrogen, was treated with sodium hydride (0.22 g of a 55–60% dispersion in mineral oil, 5.1 mmol) in one portion, at 0° C. After 45 min at 0° C., 1-iodopropane (0.55 ml) was added in one portion and the solution allowed to reach ambient temperature and stirred overnight. Solvent was removed under reduced pressure, and the crude residue partitioned between water (25 ml) and dichloromethane (25 ml). The organic phase was separated and the aqueous phase extracted with dichloromethane (3×25 ml). The combined organic layers were washed with brine (50 ml), dried ($MgSO_4$) and evaporated in vacuo. The residue was triturated with diethyl ether to give the title compound (1.74 g). Mp 160°–163° C. $^1H$ NMR (360 MHz, $CDCl_3$) δ 0.82 (3H, t, J=10.5 Hz), 0.94–1.48 (5H, m), 1.50–1.76 (5H, m), 1.79–1.90 (1H, m), 1.96–2.08 (1H, m), 2.70–2.84 (1H, m), 3.46–3.59 (1H, m), 4.22–4.35 (1H, m), 5.06–5.16 (3H, m), 5.07 (1H, d, J=12.0 Hz), 7.21–7.40 (7H, m), 7.44–7.59 (2H, m).

Step 2: 5-Cyclohexyl-1,3-dihydro-3-(R,S)-[(4 -nitrophenyloxycarbonyl)amino]-1-propyl-2H-1,4-benzodiazepin-2-one 3(R,S)-[(Benzyloxycarbonyl)amino]-5-cyclohexyl-1,3-dihydro-1-propyl-2H-1,4-benzodiazepin-2-one (1.49 g) was dissolved in hydrobromic acid (4 ml of a 30% solution in glacial acetic acid) and stirred at room temperature for 45 min. The yellow solution was then added dropwise to anhydrous diethyl ether (20 ml) at 0° C. and the resultant cream solid filtered off and washed with ether. The solid was partitioned between dichloromethane (50 ml) and 10% sodium hydroxide solution (30 ml). The organic layer was separated, dried ($Na_2SO_4$) and evaporated in vacuo to afford the crude 3(R,S)-amino-5-cyclohexyl-1,3-dihydro-1-propyl-2H-1,4-benzodiazepin-2-one (1.06 g) as a colourless viscous oil.

A solution of the crude amine (0.7 g) in anhydrous tetrahydrofuran (13 ml) under an atmosphere of nitrogen at room temperature, was treated with triethylamine (323 μl), followed by a solution of 4-nitrophenyl chloroformate (0.47 g) in anhydrous tetrahydrofuran (13 ml). The mixture was stirred for 4 h then more triethylamine (32 μl) and 4-nitrophenyl chloroformate (47 mg) were added. The mixture was stirred for a further 2 h then the solid filtered off, washed with tetrahydrofuran, and the filtrate evaporated in vacuo. The residue was azeotroped with toluene (2×20 ml) then triturated with diethyl ether to afford the title compound (553 mg). Mp 152°–155° C. $^1H$ NMR (360 MHz, $CDCl_3$) δ 0.85 (3H, t, J=7.4 Hz), 1.02–1.50 (6H, m), 1.56–1.76 (4H, m), 1.84–1.93 (1H, m), 2.00–2.08 (1H, m), 2.76–2.87 (1H, m); 3.53–3.63 (1H, m), 4.26–4.36 (1H, m), 5.14 (1H, d, J=8.0 Hz), 6.93 (1H, d, J=8.3 Hz), 7.22–7.40 (4H, m), 7.50–7.62 (2H, m), 8.18–8.26 (2H, m).

Step 3: 4-(N-tert-Butyloxycarbonyl-N'piperazinyl)-1 -nitrobenzene

To a solution of N-tert-butyloxycarbonylpiperazine (5 g) in anhydrous dimethylformamide (75 ml) containing triethylamine (7.4 ml), was added 1-fluoro-4-nitrobenzene (3.81 g). The solution was heated at 120° C. for 5 h then the solvent was evaporated in vacuo and the residue partitioned between ethyl acetate (50 ml) and water (50 ml). The organic layer was separated and the aqueous phase washed with ethyl acetate (3×50 ml). The combined organic layers were washed with water (2×50 ml), dried ($Na_2SO_4$) and evaporated in vacuo. The residue was triturated with ether and the resultant yellow solid filtered off. The solid was then chromatographed on silica gel, using a gradient elution of 0→1% methanol in dichloromethane to afford the title compound (4.45 g) as a yellow solid. $^1H$ NMR (360 MHz, $CDCl_3$) δ 1.49 (9H, s), 3.40–3.43 (4H, m), 3.59–3.62 (4H, m), 6.82 (2H, dd, J=9 and 1.8 Hz), 8.13 (2H, dd, J=9 and 1.8 Hz). MS (CI, $NH_3$) 307 ($M^+$).

Step 4: 1-Amino-4-(N-tert-butyloxycarbonyl-N'-piperazinyl)benzene

A suspension of 4-(N-tert-butyloxycarbonyl-N'-piperazinyl)-1-nitrobenzene (3.09 g) in ethanol (70 ml) was hydrogenated at 30 psi for 15 min, in the presence of a palladium on carbon catalyst (0.35 g, 11% (w/w)). The catalyst was filtered off and the residue evaporated in vacuo. The resultant oil was azeotroped with toluene (2×20 ml) followed by petrol (60/80) (20 ml) to afford the aniline (1.96 g). $^1H$ NMR (360 MHz, $CDCl_3$) δ 1.48 (9H, s), 2.96–2.98 (4H, m), 3.56–3.59 (4H, m), 6.65 (2H, d, J=8.7), 6.81 (2H, d, J=8.7 Hz). MS (CI, $NH_3$) 278 (M+1).

Step 5: N-[3(R,S)-5-Cyclohexyl-2,3-dihydro-2-oxo-1-propyl-1H-1,4-benzodiazepin-3-yl]N'-[ 4-[ (N-tert-butyloxycarbonyl-N'-piperazinyl)phenyl]urea To a stirred solution of 5-cyclohexyl-1,3-dihydro-3(R,S)-[(4 -nitrophenyloxycarbonyl)amino]-1-propyl-2H-1,4-benzodiazepin-2-one (500 mg) in anhydrous dimethylformamide (6 ml), under an atmosphere of nitrogen, was added triethylamine (173 μl). After 5 min a solution of 1-amino-4-(N-tert-butyloxycarbonyl-N'-piperazinyl) benzene (346 mg) in anhydrous dimethylformamide (6 ml) was added and the solution heated at 50° C. for 2 h. After this time the solvent was evaporated in vacuo and the residue partitioned between ethyl acetate (20 ml) and 20% aqueous acetic acid (20 ml). An undissolved white solid (260 mg) was collected and identified as the desired urea. $^1H$ NMR (360 MHz, $CDCl_3$) δ 0.81 (3H, t, J=7.4 Hz), 1.03–2.04 (21H, m), 2.78 (1H, m), 3.10 (4H, brs), 3.50–3.61 (5H, m), 4.24–4.33 (1H, m), 5.30 (1H, d, J=8 Hz), 6.60 (2H, m), 6.92–6.95 (2H, m), 7.23–7.34 (4H, m), 7.49 (1H, dd, J=8.5 and 8.5 Hz), 7.55 (1H, dd, J=8 and 1.5 Hz). MS (CI, $NH_3$) 602 ($M^+$).

Step 6: N-[3(R,S)-5-Cyclohexyl-2,3-dihydro-2-oxo-1 -propyl-1H-1,4-benzodiazepin-3-yl]N'-[4-(N-piperazinyl)phenyl]urea, hydrochloride salt Into a solution of N-[3(R,S)-5-cyclohexyl-2,3-dihydro-2-oxo-1-propyl-1H-1,4-benzodiazepin-3-yl] N'-[4-(N-tert-butyloxycarbonyl-N'-piperazinyl)phenyl]urea (260 mg) in ethyl acetate (40 ml) and dichloromethane (5 ml), at 0° C., was bubbled hydrogen chloride for 40 min. After this time the solvent was evaporated in vacuo and the residue azeotroped with ethyl acetate (3×50 ml). The resultant white solid was triturated with ether and filtered off. The title compound (156 mg) was isolated as a white solid. $^1$H NMR (360 MHz, D$_6$-DMSO) δ 0.73 (3H, t, J=7.4 Hz), 0.90–0.96 (1H, m), 1.13–1.89 (11H, m), 2.95 (1H, m), 3.21 (8H, m), 3.65 (1H, m), 4.17–4.21 (1H, m), 5.02 (1H, d, J=8.6 Hz), 6.88 (2H, d, J=9 Hz), 7.16 (1H, d, J=8.6 Hz), 7.23 (2H, d, J=9 Hz), 7.37 (1H, m), 7.63 (2H, m), 7.76 (1H, d, J=7.8 Hz), 8.84 (1H, s), 8.95 (1H, brs). MS (CI, NH$_3$) 503 (M+1).

EXAMPLE 5

N-[3(R,S)-5-Cyclohexyl-2,3-dihydro-2-oxo-1-propyl-1H-1,4-benzodiazepin-3-yl] N'-[4-(N-methyl-N'-piperazinyl)phenyl]urea To a cooled (0° C.) and stirred solution of N-[3(R,S)-5-cyclohexyl-2,3-dihydro-2-oxo-1-propyl-1H-1,4-benzodiazepin-3-yl]N'-[4-(N-piperazinyl)phenyl]urea (96 mg) in methanol (4 ml) and glacial acetic add (49 µl) was added sodium cyanoborohydride (24 mg) followed by dropwise addition of a solution of formaldehyde (37 µl of a 38% (w/v) solution in water) in methanol (2 ml). The solution was stirred at 0° C. for 20 min then at room temperature for 1 h. After this time the solvent was removed in vacuo and the residue partitioned between dichloromethane (20 ml) and saturated potassium carbonate solution (20 ml). The organic phase was separated and the aqueous layer washed with dichloromethane (2×20 ml). The combined organic layers were washed with brine (20 ml), dried (Na$_2$SO$_4$) and evaporated in vacuo to afford a white solid. This was then chromatographed on silica gel, eluting with 90:10:1:1 dichloromethane:methanol:acetic acid:water to afford the title compound (60 mg) as a white solid. $^1$H NMR (360 MHz, D$_6$-DMSO) δ 0.73 (3H, t, J=7.4 Hz), 0.89–0.95 (1H, m), 1.10–1.70 (11H, m), 2.20 (3H, s), 2.40–2.43 (4H, m), 2.94–3.01 (5H, m), 3.60–3.70 (1H, m), 4.15–4.22 (1H, m), 5.02 (1H, d, J=8.9 Hz), 6.81 (2H, d, J=9 Hz), 7.12 (1H, d, J=8.6 Hz), 7.17 (2H, d, J=9 Hz), 7.35–7.39 (1H, m), 7.61–7.63 (2H, m), 7.76 (1H, d, J=7.8), 8.74 (1H, s). MS (CI, NH$_3$) 517 (M+1).

EXAMPLE 6

N-[3(R,S)-5-Cyclohexyl-2,3-dihydro-2-oxo-1-propyl-1H-1,4-benzodiazepin-8-yl] N'-[3-(N-methyl-N'-piperazinyl)phenyl]urea Step 1: 3-(N-Methyl-N'-piperazinyl)-1-nitrobenzene A mixture of N-methylbis(2-chloroethyl)-amine hydrochloride (9.8 g) and 3-nitroaniline (7.0 g) in 1-butanol (100 ml) was heated at reflux for 60 h then cooled to room temperature. Sodium carbonate (2.8 g) was added and the mixture heated at reflux for a further 18 h. The mixture was cooled to 0° C. and filtered. The solid was collected, washed with anhydrous ether then partitioned between dichloromethane (200 ml) and sodium hydroxide solution (1M, 150 ml). The organic layer was separated and the aqueous phase washed once more with dichloromethane (200 ml). The combined organic layers were dried (K$_2$CO$_3$) and evaporated in vacuo. The resultant residue was chromatographed on silica gel, using dichloromethane:methanol (96:4) as the eluant, to afford an orange oil. The oil crystallized on standing and the resultant solid was triturated with petrol (60/80) to give the desired piperazine (5.64 g). $^1$H NMR (360 MHz, CDCl$_3$) δ 2.37 (3H, s), 2.58 (4H, t, J=5 Hz), 3.30 (4H, t, J=5 Hz), 7.18 (1H, dd, J=9 and 3 Hz), 7.35 (1H, t, J=8 Hz), 7.64 (1H, dd, J=9 and 2 Hz), 7.71 (1H, d, J=2 Hz). MS (CI, NH$_3$) 222 (M+1).

Step 2: 1-Amino-3-(N-methyl-N'-piperazinyl)benzene

A solution of 3-(N-methyl-N-piperazinyl)-1-nitrobenzene (1.17 g) in ethanol (40 ml) was hydrogenated at 25 psi for 20 min in the presence of a palladium on carbon catalyst (200 mg, 17% (w/w)). The catalyst was filtered off and the solvent evaporated in vacuo. The residue was chromatographed on silica gel, using a gradient elution of petrol:ether (1:1) followed by dichloromethane:methanol (95:5) to give a colourless oil, which was azeotroped with toluene (20 ml) then left at 0° C. overnight. After this time the oil had crystallized, and after trituration with petrol (60/80) the desired aniline (0.86 g) was isolated as a white solid. $^1$H NMR (360 MHz, CDCl$_3$) δ 2.34 (3H, s), 2.55 (4H, t, J=5 Hz), 3.18 (4H, t, J=5 Hz), 3.60 (2H, brs), 6.20 (1H, dd, J=8 and 2 Hz), 6.25 (1H, t, J=2 Hz), 6.36 (1H, dd, J=8 and 2 Hz), 7.04 (1H, t, J=8 Hz). MS (CI, NH$_3$) 192 (M+1).

Step 3: N-[3(R,S)-5-Cyclohexyl-2,3-dihydro-2-oxo-1-propyl-1H-1,4-benzodiazepin-3-yl] N'-[ 3-(N-methyl-N'-piperazinyl)phenyl]urea To a solution of 1-amino-3-(N-methyl-N'-piperazinyl) benzene (140 mg) in anhydrous tetrahydrofuran (20 ml) at 0° C., under an atmosphere of nitrogen, was added triphosgene (71 mg). After 2 min, triethylamine (260 µl) was added dropwise and the mixture stirred at 0° C. for 5 min then at room temperature for 10 min. The mixture was then cooled back to 0° C. and a solution of crude 3(R,S)-amino-5-cyclohexyl-1,3-dihydro-1-propyl-2H-1,4-benzodiazepin-2-one (150 mg) in anhydrous tetrahydrofuran (5 ml) dropwise. The mixture was stirred at 0° C. for 5 min then at room temperature for 10 min. The mixture was filtered and the filtrate evaporated in vacuo. The residue was partitioned between ethyl acetate (30 ml) and water (30 ml) and an undissolved solid filtered off. The organic phase from the filtrate was separated and the aqueous phase washed once more with ethyl acetate (10 ml). The combined organic layers were washed with brine (20 ml), dried (Na$_2$SO$_4$) and evaporated in vacuo. The residue was chromatographed on silica gel using 95:5:1 dichloromethane:methanol:ammonia as the solvent. After trituration with ether the title urea (77 mg) was isolated as a white solid. Mp 255°–257° C. $^1$H NMR (360 MHz, D$_6$-DMSO) δ 0.73 (3H, t, J=7.3 Hz), 0.92 (1H, m), 1.07–1.90 (11H, m), 2.19 (3H, s), 2.39–2.42 (4H, m), 2.95 (1H, m), 3.02–3.05 (4H, m), 3.62–3.67 (1H, m), 4.16–4.22 (1H, m), 5.02 (1H, d, J=8.6 Hz), 6.49 (1H, dd, J=8 and 1.5 Hz), 6.01 (1H, d, J=8 and 1.5 z), 7.03 (1H, t, J=8 Hz), 7.11 (H, m), 7.21 (1H, d, J=8.5 Hz), 7.39 (1H, m), 7.62–7.63 (2H, m), 7.76 (1H, d, J=7.9 Hz), 8.82 (1H, s).

EXAMPLE 7

N-[3(R,S)-2,3-Dihydro-1-methyl-5-(4-methylpiperidin-1-yl)-2-oxo-1H-1,4-benzodiazepin-3-yl]N'-[3-(N-methyl-N'-piperazinyl)phenyl]urea Step 1: Methyl-2-(N-bromoacetyl-N-methylamino)benzoate A solution of bromoacetyl bromide (209 g) in dichloromethane (200 ml) was added dropwise to a cooled (ice bath) solution of methyl N-methylanthranilate (168 g) in dichloromethane (1400 ml). A solution of sodium hydroxide (59 g) in water (400 ml) was added dropwise to this ice cold solution then after addition the reaction mixture was stirred at room temperature for 20 h. The organic phase was separated and washed with 1M hydrochloric acid (500 ml), brine (300 ml), saturated sodium hydrogen carbonate solution (400 ml), dried ($Na_2SO_4$) then evaporated to afford the required product as a solid (255 g, 92%). Mp 80°–82° C. $^1$H NMR (360 MHz, $CDCl_3$) δ 3.23 (3H, s), 3.54 (1H, d, J=11 Hz), 3.60 (1H, d, J=11 Hz), 3.90 (3H, s), 7.40 (1H, d, J=8 Hz), 7.51 (1H, dd, J=8 and 8 Hz), 7.65 (1H, dd, J=8 and 8 Hz), 8.04 (1H, d, J=8 Hz).

Step 2: 1-Methyl-1,2,3,4-tetrahydro-3H-1,4-benzodiazepin-2,5-dione

Ammonia gas was bubbled through an ice-cooled solution of methyl 2-(N-bromoacetyl-N-methylamino)benzoate (255 g) in methanol (1600 ml) until saturated. The cooling bath was removed and the reaction mixture left standing at room temperature for 18 h. The precipitate was collected to afford the required product (79 g). The filtrate was evaporated and the residue partitioned between dichloromethane (300 ml) and 10% citric acid solution (200 ml). The organic layer was separated, washed with brine (200 ml), dried ($Na_2SO_4$) then evaporated to give a solid which was recrystallised from dichloromethane/petroleum ether (60/80) to afford further product (32.5 g). Total yield= 111.5 g. Mp 190°–193° C. $^1$H NMR (360 MHz, $CDCl_3$) δ 3.42 (3H, s), 3.80 (2H, brs), 6.80 (1H, s), 7.24 (1H, d, J=8 Hz), 7.32 (1H, dd, J=8 and 8 Hz); 7.57 (1H, dd, J=8 and 8 Hz), 7.90 (1H, d, J=8 Hz).

Step 3: 1,2-Dihydro-1-methyl-5-(4-methylpiperidin-1-yl)-3H-1,4-benzodiazepin-2-one To a solution of 1-methyl-1,2,3,4-tetrahydro-3H-1,4-benzodiazepin-2,5-dione (5 g) in anhydrous dichloromethane (150 ml) was added phosphorous pentachloride (6.74 g) in anhydrous dichloromethane (350 ml) over a period of 30 min. The reaction mixture was stirred at ambient temperature for 1.5 h. The solvent was evaporated in vacuo and the residue redissolved in anhydrous dichloromethane (200 ml). After cooling to 0° C., a solution of 4-methylpiperidine (10.9 ml) in anhydrous dichloromethane (100 ml) was added dropwise. When the addition was complete, the reaction mixture was allowed to warm to ambient temperature and left to stir for 2 h. The solution was washed with saturated sodium bicarbonate solution (300 ml). The organic layer was dried ($Na_2SO_4$) and treated with decolourising charcoal (5 spatulas) and silica gel (10 spatulas). After filtering, the solvent was evaporated in vacuo. The residue was redissolved in dichloromethane (100 ml) and extracted with citric acid solution (10%, 4×25 ml). The combined aqueous layers were basified (4M NaOH solution) and extracted with dichloromethane (6×50 ml). These organic extracts were combined, dried ($K_2CO_3$) and evaporated in vacuo to give title compound (4.0 g) as a beige solid. Mp 106°–108° C. $^1$H NMR (360 MHz, $CDCl_3$) δ 0.97 (3H, d, J=6.3 Hz), 1.10–1.22 (1H, m), 1.26–1.42 (1H, m), 1.55–1.63 (2H, m), 1.70–1.77 (1H, m), 2.62–2.70 (1H, m), 2.76–2.86 (1H, m), 3.35 (3H, s), 3.47–3.57 (2H, m), 3.80–3.90 (1H, m), 4.23 (1H, d, J=14.4 Hz), 7.18–7.30 (2H, m), 7.45–7.56 (2H, m).

Step 4: 1,2-Dihydro-1-methyl-5-(4-methylpiperidin-1-yl)- 3-oximido-3H-1,4-benzodiazepin-2-one A solution of 1,2-dihydro-1-methyl-5-(4-methylpiperidin-1-yl)-3H-1,4-benzodiazepin-2-one (3.5 g) in anhydrous toluene (100 ml) was cooled to −20° C. under an atmosphere of nitrogen, and potassium-tert-butoxide (3.95 g) was added portionwise over 2 min. After stirring at −20° C. for 30 min, isopentyl nitrite (2.1 ml) was added dropwise to the red mixture. The reaction mixture was stirred at −20° C. for 5 h and then allowed to warm to ambient temperature. The mixture was poured onto a rapidly stirred mixture of ethyl acetate (200 ml) and water (50 ml) containing citric acid (2.45 g). This mixture was stirred vigorously for 5 min and then neutralized to pH7 using saturated potassium carbonate solution. The organic layer was separated and the aqueous layer extracted with ethyl acetate (3×100 ml). The combined organic phases were dried ($Na_2SO_4$) and evaporated in vacuo to give an orange solid. This was triturated with diethyl ether and the resulting solid collected by filtration to give the title compound (2.39 g) as a beige solid. Mp 225°–228° C. $^1$H NMR (360 MHz, $D_6$-DMSO) δ 0.90–1.15 (4H, m) 1.20–1.36 (1H, m), 1.54–1.76 (3H, m), 2.77–3.01 (2H, m), 3.26 (3H, s), 3.69–4.24 (2H, m), 7.24–7.32 (1H, m), 7.38–7.43 (1H, m), 7.46–7.58 (2H, m), 9.93 and 10.16 (1H, 2 x s).

Step 5: 1,2 Dihydro-1-methyl-5-(4-methylpiperidin-1-yl)-3-O-ethylaminocarbonyl)oximido-3H-1,4-benzodiazepin-2-one To a suspension of 1,2-dihydro-1-methyl-5-(4-methylpiperidin-1-yl)-3-oximido-3H-1,4-benzodiazepin-2-one (0.5 g) in anhydrous tetrahydrofuran (20 ml) was added triethylamine (0.23 ml) followed by ethyl isocyanate (0.2 ml) dropwise. This mixture was heated at 60° C. under an atmosphere of nitrogen for 4.5 h. The solvent was evaporated in vacuo to give the title compound (0.62 g) as a pale yellow foam. $^1$H NMR (360 MHz, $CDCl_3$) δ 1.00 (3H, brs), 1.13 (3H, t, J=7.2 Hz), 1.22–1.42 (2H, m), 1.54–1.90 (3H, m), 2.78–3.30 (4H, m), 3.44 (3H, s), 3.56–3.78 (1H, m), 4.54–4.86 (1H, m), 6.37–6.45 (1H, m), 7.21–7.38 (3H, m), 7.46–7.54 (1H, m). TLC (silica, dichloromethane:methanol 90:10) Rf= 0.66 and 0.71.

Step 6: N-[3(R,S)-2,3-Dihydro-1-methyl-5-(4-methylpiperidin-1-yl)-2-oxo-1H-1,4-benzodiazepin-3-yl] N'-[3-(N methyl-N'-piperazinyl)phenyl]urea To a solution of 1,2-dihydro-1-methyl-5-(4- methylpiperidin-1 -yl)-3-(O-ethylaminocarbonyl)oximido-3H-1,4-benzodiazepin-2-one (0.62 g) in methanol (30 ml) was added 10% palladium on carbon (0.2 g, 32% (w/w)). The mixture was hydrogenated at 40 psi for 2 h. Further 10% palladium on carbon (0.1 g, 16% (w/w)) was added and the mixture hydrogenated at 40 psi for another 1 h. The catalyst was then filtered off and washed with methanol. The solvent was evaporated in vacuo to give the amine (0.48 g) as a pale yellow gum which was used without further purification.

To a solution of 1-amino-3-(N-methyl-N'-piperazinyl)benzene (Example 2, Step 2) (0.48 g) in anhydrous tetrahydrofuran (30 ml) cooled to 0° C. under an atmosphere of nitrogen was added triphosgene (0.25 g) in one portion. Triethylamine (1.0 ml) was added dropwise to ensure a basic solution. After stirring at 0° C. for 30 min a solution of the amine (0.48 g) in anhydrous tetrahydrofuran (10 ml) was added dropwise. The mixture was stirred at 0° C. for 5 min and then allowed to warm to ambient temperature and stirred for 10 min. The solvent was evaporated in vacuo and the residue partitioned between ethyl acetate (50 ml) and water (50 ml). The undissolved solid was collected by filtration and purified by chromatographing on silica gel using 95:5:1, dichloromethane:methanol:aqueous ammonia solution increasing the ratio to 90:10:1, to give the title compound (0.55 g) as a colourless solid. Mp 160° C. (dec.). $^1$H NMR (360 MHz, $CDCl_3$) δ 0.95 (3H, d, J=6.2 Hz), 1.05–1.21 (1H, m), 1.28–1.37 (1H, m), 1.46–1.62 (2H, m), 1.64–1.74 (1H, m), 2.45 (3H, s), 2.57–2.80 (6H, m), 3.25–3.35 (4H, m), 3.41 (3H, s), 3.47–3.60 (1H, m), 3.86–3.96 (1H, m), 5.26 (1H, d, J=7.8 Hz), 6.52–6.58 (2H, m), 6.65 (1H, d, J=7.9 Hz), 6.98 (1H, brs), 7.11 (1H, t, J=8.1 Hz), 7.16–7.20 (1H, m), 7.21–7.33 (2H, m), 7.47–7.55 (2H, m)

EXAMPLE 8

N-[3(R,S)-5-Cycloheptyl-2,3-dihydro-1-methyl-2-oxo-1H-1,4-benzodiazepin-3-yl]N'-[3-(N-morpholinomethyl)phenyl]urea Step 1: 3(R,S)-[(Benzyloxycarbonyl)amino]-5-cycloheptyl-1,3-dihydro-1-methyl-2H-1,4-benzodiazepin-2-one 3(R,S)-[(Benzyloxycarbonyl)amino]-5-cycloheptyl-1,3-dihydro-2H-1,4-benzodiazepin-2-one (Example 1, Step 3, 500 mg) in anhydrous toluene (40 ml) was heated to reflux. A solution of dimethylformamide dimethyl acetal (786 µl) in anhydrous toluene (10 ml) was added dropwise and the mixture was heated at reflux for a further hour. The solvent was evaporated and the residue triturated with diethyl ether to afford the title compound (441 mg) as a colourless solid. $^1$H NMR (360 MHz, CDCl$_3$) δ 1.24–1.90 (11H, m), 2.00–2.14 (1H, m), 2.90–3.00 (1H, m), 3.40 (3H, s), 5.04–5.18 (3H, m), 6.52 (1H, d, J=7.5 Hz), 7.24–7.60 (9H, m). TLC (silica, petrol (60/80): ethyl acetate 2:1). Rf= 0.30.

Step 2: 3-(N-Morpholinomethyl)-1-nitrobenzene

A solution of morpholine (2.0 g) in anhydrous acetone (100 ml) was treated with potassium carbonate (4.8 g) and 3-nitrobenzyl bromide (5.0 g). The mixture was stirred at room temperature for 48 h. The solvent was evaporated and the residue partitioned between ethyl acetate (100 ml) and water (50 ml). The aqueous layer was washed with ethyl acetate (2×80 ml). The combined organics were dried (Na$_2$SO$_4$), evaporated and the residue chromatographed on silica gel with 3:1 petrol:ethyl acetate as eluant to afford the title compound (2.6 g) as a pale yellow solid. $^1$H NMR (250 MHz, CDCl$_3$) δ 2.42–2.54 (4H, m), 3.61 (2H, s), 3.70–3.80 (4H, m), 7.50 (1H, t, J=7.5 Hz), 7.69 (1H, d, J=7.5 Hz), 8.09–8.18 (1H, m), 8.24 (1H, s). TLC (silica, petrol (60/80):ethyl acetate 3:1). Rf= 0.50.

Step 3: 1-Amino-3-(N-morpholinomethyl)benzene 3-(N-Morpholinomethyl)-1-nitrobenzene (1.25 g) in ethanol (50 ml) was treated with 10% palladium on carbon (125 mg, 10% (w/w)). The mixture was hydrogenated at 25 psi for 7 min. The catalyst was filtered off and the solvent evaporated. The residue was chromatographed on silica gel with 2:1 petrol:ethyl acetate as eluant to afford the title compound (0.75 g). $^1$H NMR (360 MHz, CDCl$_3$) δ 2.40–2.50 (4H, m), 3.42 (2H, s), 3.64 (2H, brs), 3.68–3.80 (4H, m), 6.57 (1H, dd, J=7.2 and 1.6 Hz), 6.69–6.71 (2H, m), 7.07–7.11 (1H, m). TLC (silica, petrol (60/80):ethyl acetate 2:1 ). Rf= 0.30.

Step 4: N-[3(R,S)-5-Cycloheptyl-2,3-dihydro-1-methyl-2-oxo-1H-1,4-benzodiazepin-3-yl]N'-[3-(N-morpholinomethyl)phenyl] urea 3(R,S)-[(Benzyloxycarbonyl)amino]-5-cycloheptyl-1,3-dihydro-1-methyl-2H-1,4-benzodiazepin-2-one (435 mg) was treated with a solution of 30% hydrogen bromide in glacial acetic add (10 ml) and stirred for 20 min at room temperature. The mixture was then added dropwise onto cold (0° C.) diethyl ether (50 ml). A white solid precipitated which was filtered off. The solid was treated with 10% sodium hydroxide solution (50 ml), then extracted with ethyl acetate (80 ml). The organic layer was separated, dried (Na$_2$SO$_4$) and evaporated to give crude 3(R,S)-amino-5-cycloheptyl-1,3-dihydro-1 -methyl-2H-1,4-benzodiazepin-2-one as a colourless oil.

1-Amino-3-(N-morpholinomethyl)benzene (180 mg) in anhydrous tetrahydrofuran (40 ml) was cooled to 0° C. whereupon triphosgene (92 mg) was added. The mixture was stirred at 0° C. for 2 min, then triethylamine (391 µl) was added portionwise until pH8. The mixture was then stirred for a further 5 min, allowed to warm to 15° C., and then re-cooled to 0° C. Then a solution of 3(R,S)-amino-5-cycloheptyl-1,3-dihydro-1methyl-2H-1,4-benzodiazepin-2-one (181 mg) in anhydrous tetrahydrofuran (7 ml) was added dropwise over 5 min. The mixture was stirred at 0° C. for 5 min, allowed to warm to room temperature and then stirred for a further 2 h. The undissolved material was removed by filtration. The solvent was evaporated in vacuo and the residue partitioned between ethyl acetate (50 ml) and water (20 ml). The organic phase was separated, dried (Na$_2$SO$_4$) and evaporated. The crude solid was recrystallised from ethyl acetate to afford the title compound as a colourless solid (89 mg). Mp 190°–192° C. $^1$H NMR (360 MHz, CDCl$_3$) δ 1.24–1.94 (11H, m), 2.04–2.16 (1H, m), 2.40–2.48 (4H, m), 2.90–3.00 (1H, m), 3.42 (3H, s), 3.45 (2H, s), 3.66–3.73 (4H, m), 5.35 (1H, d, J=8 Hz), 6.61 (1H, d, J=8 Hz), 6.81 (1H, s), 6.99–7.06 (1H, m), 7.18–7.34 (4H, m), 7.36 (1H, s), 7.46–7.62 (2H, m).

EXAMPLE 9

N-(R,S)-5-Cycloheptyl-2,3-dihydro-1-methyl-2-oxo-1H-1,4-benzodiazepin-3-yl]N'-[3-(2-(N-morpholino)-ethoxy)phenyl]urea Step 1: 3-[2-(N-Morpholino)ethoxy]-1-nitrobenzene A solution of 3-nitrophenol (3.0 g) in anhydrous dioxane (100 ml) was treated with caesium carbonate (18 g) and N-(2-chloroethyl)morpholine (20 g). The mixture was heated at 80° C. for 16 h. The undissolved material was filtered off. The solvent was evaporated in vacuo and the residue partitioned between ethyl acetate (80 ml) and water (50 ml). The organic phase was separated, dried (Na$_2$SO$_4$) and evaporated. The residue was chromatographed on silica gel with petrol (60/80):ethyl acetate (1:1) as the eluant to afford the title compound (3.2 g) as a yellow oil. $^1$H NMR (250 MHz, CDCl$_3$) δ 2.55–2.65 (4H, m), 2.84 (2H, t, J=5 Hz), 3.72–3.78 (4H, m), 4.20 (2H, t, J=5 Hz), 7.21–7.29 (1H, m), 7.42 (1H, t, J=7.5 Hz), 7.72–7.78 (1H, m), 7.80–7.88 (1H, m). TLC (silica, ethyl acetate) Rf= 0.36.

Step 2: 1-Amino-3-[2-(N-morpholino)ethoxy]benzene

3-[2-(N-Morpholino)ethoxy]-1-nitrobenzene (1.6 g) in ethanol (30 ml) was treated with 10% palladium on carbon (159 mg, 10% (w/w)). The mixture was hydrogenated at 25 psi for 15 min. The catalyst was filtered off and the solvent evaporated. The residue was chromatographed on silica gel with ethyl acetate as the eluant to afford the title compound (1.05 g). $^1$H NMR (250 MHz, CDCl$_3$) δ 2.54–2.63 (4H, m), 2.80 (2H, t, J=6.3 Hz), 3.65 (2H, brs), 3.72–3.78 (4H, m), 4.09 (2H, t, J=6.3 Hz), 6.21–6.36 (3H, m), 7.05 (1H, t, J=7.5 Hz). TLC (silica, ethyl acetate) Rf= 0.18.

Step 3: N-[3(R,S)-5-Cycloheptyl-2,3-dihydro-1-methyl-2-oxo-1H-1,4-benzodiazepin-3-yl]N'-[3-(2-(N-morpholino)ethoxy)phenyl]urea 1-Amino-3-[ 2-(N-morpholino)ethoxy]benzene (323 mg) in anhydrous tetrahydrofuran (30 ml) was cooled to 0° C. whereupon triphosgene (143 mg) was added. The mixture was stirred at 0° C. for 2 min, then triethylamine (607 µl) was added portionwise until pH8. The mixture was then stirred for a further 5 min, allowed to warm to 15° C., and then re-cooled to 0° C. Then a solution of 3(R,S)-amino-5-cycloheptyl-1,3-dihydro-1-methyl-2H- 1,4-benzodiazepin-2-one (282 mg) in anhydrous tetrahydrofuran (10 ml) was added dropwise over 5 min. The mixture was stirred at 0° C.

for 5 min, allowed to warm to room temperature and stirred for a further 1 h. The undissolved material was removed by filtration. The solvent was evaporated in vacuo and the residue partitioned between ethyl acetate (50 ml) and water (20 ml). The organic phase as separated, dried ($Na_2SO_4$) and evaporated. The residue was chromatographed on silica gel with a gradient elution of 0→3% methanol in dichloromethane to afford the title compound (360 mg). Mp 204°–205° C. $^1$H NMR (360 MHz, $D_6$-DMSO) δ 1.10–1.86 (11H, m), 1.90–2.02 (1H, m), 2.40–2.48 (4H, m), 2.65 (2H, t, J=5.7 Hz), 3.08–3.20 (1H, m), 3.30 (3H, s), 3.54–3.60 (4H, m), 3.99 (2H, t, J=5.7 Hz), 5.04 (1H, d, J=8.4 Hz), 6.48 (1H, dd, J=7.7Hz and 2.0 Hz), 6.75 (1H, d, J=9.4 Hz), 7.06–7.15 (2H, m), 7.26 (1H, d, J=8.4 Hz), 7.37 (1H, t, J=6.7 Hz), 7.54 (1H, d, J=8.3 Hz), 7.63 (1H, t, J=7.0 Hz), 7.76 (1H, dd, J=7.9 Hz and 1.4 Hz), 8.98 (1H, s).

EXAMPLE 10

N-[3(R)-5-Cyclohexyl-2,3-dihydro-1-methyl-2-oxo-1H-1,4-benzodiazepin-3-yl]N'-[3-(2-(N-morpholino)-ethoxy)phenyl]urea Step 1: 3(R,S)-Amino-5-cyclohexyl-1,3-dihydro-1-methyl-2H-1,4-benzodiazepin-2-one A mixture of 3(R,S)-[(benzyloxycarbonyl)amino]-5-cyclohexyl-1,3-dihydro-1-methyl-2H-1,4-benzodiazepin-2-one (3.0 g) and hydrobromic add (45% in acetic add, 6.2 ml) was stirred for 1 h at room temperature under an atmosphere of nitrogen. The mixture was then diluted with cold anhydrous diethyl ether (40 ml) and stirred at 0° C. for 45 min. The white precipitate was collected by filtration, washed with cold diethyl ether (4×30 ml) and then dissolved in a mixture of water (30 ml) and aq. sodium hydroxide (2M, 15 ml). The basic aqueous phase was extracted with ethyl acetate (3×70 ml) and the combined organic layers were washed with brine (30 ml), dried ($Na_2SO_4$) and concentrated. The residue was chromatographed on silica gel, using 94:6, dichloromethane:methanol as the eluant, to afford the title compound (1.6 g) as a pale pink solid. Mp 133°–136° C. $^1$H NMR (360 MHz, $CDCl_3$) δ 1.02–1.40 (4H, m), 1.47–1.56 (1H, m), 1.61–1.74 (3H, m), 1.84–1.91 (1H, m), 1.96–2.06 (1H, m), 2.17 (2H, brs), 2.70–2.80 (1H, m), 3.39 (3H, s), 4.29 (1H, s), 7.20–7.27 (2H, m), 7.44–7.54 (2H, m).

Step 2: 3(R,S)-[2(R)-(tert-Butyloxycarbonyl)amino-3-phenylpropionylamino]-5-cyclohexyl-1,3-dihydro-1-methyl-2H-1,4-benzodiazepin-2-one To a solution of 3(R,S)-amino-5-cyclohexyl-1,3-dihydro-1-methyl-2H-1,4-benzodiazepin-2-one (4 g) in anhydrous dimethylformamide (35 ml), under an atmosphere of nitrogen, was added in succession Boc-D-phenyl-alanine (4.11 g), 1-hydroxybenzotriazole trihydrate (2.09 g) and 1-ethyl-3-[3-(dimethylamino)propyl]carbodiimide hydrochloride (2.97 g). Triethylamine (2.16 ml) was then added and the resulting suspension was stirred at ambient temperature for 20 min. The solvent was removed under reduced pressure and the residue was partitioned between ethyl acetate (50 ml) and 10% citric add solution (50 ml). The organic phase was separated and the aqueous phase extracted with ethyl acetate (3×50 ml). The combined organic phases were washed with 10% sodium hydroxide solution (50 ml), water (50 ml) and brine (50 ml), dried ($MgSO_4$) and evaporated in vacuo. The residue was chromatographed on silica gel, using 1:1 petrol:ethyl acetate as the eluant, to afford the product (7.26 g), mp 95°–98° C. $^1$H NMR (360 MHz, $CDCl_3$) δ 0.99–1.11 (1H, m), 1.16–1.72 (7H, m), 1.40 (9H, s), 1.83–1.92 (1H, m), 1.98–2.06(1H, m), 2.73–2.83 (1H, m), 3.10–3.24 (2H, m), 3.38 (3H, s), 4.53 (1H, brs), 4.98 (1H, brs), 5.28–5.34 (2H, m), 7.19–7.32 (7H, m), 7.49–7.58 (2H, m).

Step 3: (+)-3(R)-(2(R)-Amino-3-phenylpropionylamino)-5-cyclohexyl-1,3-dihydro-1-methyl-2H-1,4-benzodiazepin-2-one 3(R,S)-[2(R)-(tert-Butyloxycarbonyl)amino-3-phenylpropionylamino]-5-cyclohexyl-1,3-dihydro-1-methyl-2H-1,4-benzodiazepin-2-one (4.7 g) was dissolved in ethyl acetate (20 ml) and cooled to 0° C. This solution was then saturated with hydrogen chloride gas. After 1.5 h, the resulting precipitate (which was shown to be the undesired diastereoisomer, Rf= 0.04 ethyl acetate), was removed by filtration and the filtrate evaporated. The solid residue was partitioned between ethyl acetate (25 ml) and 10% sodium carbonate solution (20 ml). The organic phase was separated and the aqueous extracted with ethyl acetate (2×25 ml). The combined organic phases were dried ($Na_2SO_4$) and evaporated in vacuo. The residue was chromatographed on silica gel using a gradient elution of 0–20% methanol in ethyl acetate to afford the title compound (1.66 g). Mp 100°–103° C. $^1$H NMR (360 MHz, $CDCl_3$) δ 1.00–1.39 (4H, m), 1:50–1.72 (4H, m), 1.84–1.92 (1H, m), 2.00–2.07 (1H, m), 2.72–2.84 (2H, m), 3.28 (1H, dd, J=13.8 and 4.0 Hz), 3.40 (3H, s), 3.69 (1H, dd, J=9.8 and 4.1 Hz), 5.36 (1H, d, J=8.3 Hz), 7.21–7.36 (7H, m), 7.47–7.58 (2H, m), 8.66 (1H, d, J=8.3 Hz). $[α]_D^{23}$+32.7° (c= 0.58, $CH_3OH$).

Step 4: (+)-N-[1(R)-2-[(3(R)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea A solution of (+)-3(R)-(2(R)-amino-3-phenylpropionylamino)-5-cyclohexyl-1,3-dihydro-1-methyl-2H-1,4-benzodiazepin-2-one (1.6 g) in anhydrous dichloromethane (10 ml) was treated with phenyl isothiocyanate (0.5 ml), and then heated on the steam bath for 30 min. The solvent was evaporated in vacuo and the residue was chromatographed on silica gel with 1:1, ethyl acetate:petrol as the eluant, to afford the product (2.1 g) as a pale yellow solid. Mp 129°–132° C. $^1$H NMR (360 MHz, $CDCl_3$) δ 0.95–1.07 (1H, m), 1.15–1.37 (3H, m), 1.45–1.69 (4H, m), 1.81–1.88 (1H, m), 1.93–2.00 (1H, m), 2.70–2.80 (1H, m), 3.24–3.41 (2H, m), 3.38 (3H, s), 5.23 (1H, d, J=7.3 Hz), 5.31–5.40 (1H, m), 6.67 (1H, 7.0 Hz), 6.87–7.02 (2H, m), 7.20–7.35 (9H, m), 7.46–7.52 (2H, m), 7.65 (1H, s). $[α]^{25}_D$+27.3° (c= 0.31, $CH_2Cl_2$).

Step 5: (+)-3(R)-Amino-5-cyclohexyl-3-dihydro-1-methyl-2H-1,4-benzodiazepin-2-one (+)-N-[ 1(R)-2-[(3(R)-5-Cyclohexyl-2,3-dihydro-1-methyl-2 -oxo-1H-1,4-benzodiazepin-3-yl)amino]-2-oxo-1-(phenylmethyl) ethyl]N'-phenyl thiourea (4.5 g) was dissolved in trifluoroacetic acid (25 ml) and stirred at ambient temperature for 30 min. The trifluoroacetic acid was removed under reduced pressure and the residue azeotroped with dichloromethane (2×20 ml) and toluene (2×20 ml). The residue was chromatographed on silica gel using 90:10:0.1:0.1, dichloromethane:methanol:acetic acid:water as the eluant, to afford an orange gum. This was dissolved in ethyl acetate (150 ml), cooled to 0° C., and treated with 10% sodium carbonate solution (15 ml). After diluting with water (25 ml) and stirring for 1 min, the organic layer was separated and the aqueous re-extracted with ethyl acetate (2×50 ml). The combined organics were dried ($Na_2SO_4$) and evaporated in vacuo to afford the title compound (1.56 g) as a solid with 99% e.e. Mp 133°–136° C. $^1$H NMR (360 MHz, $CDCl_3$) δ 1.01–1.39 (4H, m), 1.50–1.54 (1H, m), 1.60–1.70 (3H, m), 1.84–1.92 (1H, m), 1.96–2.04 (1H, m), 2.36 (2H, brs), 2.70–2.80 (1H, m), 3.41 (3H, s), 4.32 (1H, s), 7.22–7.28 (2H, m), 7.46–7.58 (2H, m). [α]$_D$+33.2° C. (c= 0.66, CH$_3$OH).

Step 6: N-[3(R)-5-Cyclohexyl-2,3-dihydro-1-methyl-2-oxo-1H-1,4-benzodiazepin-3-yl]N'-[3-(2-(N-morpholino)-ethoxy) phenyl]urea 1-Amino-3-[ 2-(N-morpholino)ethoxy)]benzene (241 mg) was dissolved in anhydrous tetrahydrofuran (40 ml) and cooled to 0° C. under an atmosphere of nitrogen. Triphosgene (106 mg) was added in one portion and the mixture was stirred for 5 min. The mixture was then treated with triethylamine (0.45 ml) dropwise over a period of 5 min. The mixture was allowed to warm to 10° C. over a period of 15 min and was then re-cooled to 0° C. 3(R)-Amino-5-cyclohexyl-1,3-dihydro-1-methyl-2H-1,4-benzodiazepin-2-one (0.2 g) was dissolved in anhydrous tetrahydrofuran (10 ml) and added to the reaction dropwise. The mixture was stirred at ambient temperature for 15 min. The precipitated solid was removed by filtration and washed with tetrahydrofuran. The filtrate was evaporated and partitioned between ethyl acetate (50 ml) and water (25 ml). The organic layer was separated and then dried (Na$_2$SO$_4$). The solvent was evaporated in vacuo and the residue chromatographed on silica gel using a gradient elution of 1→10% methanol in dichloromethane.

The desired urea (220 mg) was isolated as a white solid. Mp 174°–176° C. $^1$H NMR (360 MHz, D$_6$-DMSO) a 0.82–0.93 (1H, m), 1.09–1.89 (9H, m), 2.44 (4H, m), 2.64 (2H, t, J=5.7 Hz), 2.90–2.96 (1H, m), 3.29 (3H, m), 3.55 (4H, m), 3.99 (2H, t, J=5.7 Hz), 5.05 (1H, d, J=8.3 Hz), 6.48 (1H, dd, J=8.0 and 2.1 Hz), 6.75 (1H, m), 7.11 (2H, m), 7.26 (1H, d, J=8.4 Hz), 7.38 (1H, dd, J=7.1 and 7.1 Hz), 7.54 (1H, m), 7.62 (1H, dd, J=7.1 and 7.1 Hz), 7.75 (1H, m), 8.98 (1H, s).

EXAMPLE 11

N-[3(R,S)-5-Cycloheptyl-2,3-dihydro-1-(2-methylpropyl)-2-oxo-1H-1,4-benzodiazepin-3-yl]N'-[3-(N-methyl-N'-piperazinyl) phenyl]urea Step 1: 3(R,S)-[(Benzyloxycarbonyl)amino]-5-cycloheptyl-1,3-dihydro-1-(2-methylpropyl)-2H-1,4-benzodiazepin-2-one To a solution of 3(R,S)-[(benzyloxycarbonyl)amino]-5-cycloheptyl-1,3-dihydro-2H-1,4-benzodiazepin-2-one (1.26 g) at 0° C., under an atmosphere of nitrogen, was added sodium hydride (125 mg of a 50% dispersion in mineral oil). After stirring for 1 h at 0° C. 2-methylpropyl iodide (399 µl) was added and the mixture allowed to warm to ambient temperature over 3 h. More sodium hydride (16 mg of a 50% dispersion in mineral oil) followed by 2-methylpropyl iodide (40 µl) was added and the solution stirred at room temperature for 18 h. More sodium hydride (103 mg of a 50% dispersion in mineral oil) followed by 2-methylpropyl iodide (210 µl) was added and the solution stirred for 4 h at room temperature. The solvent was then evaporated in vacuo and the residue partitioned between dichloromethane (30 ml) and water (30 ml). The organic phase was separated and the aqueous layer washed further with dichloromethane (3×20 ml). The combined organic layers were washed with brine (20 ml), dried (MgSO$_4$) and evaporated under reduced pressure. The residue was azeotroped with toluene (2×20 ml), then chromatographed on silica gel using 4:1 petrol:ethyl acetate as the eluant. The product was isolated as a viscous oil which solidified on addition of petrol:ethyl acetate (4:1) (20 ml). After evaporation of the solvent the resultant solid was triturated with petrol (60/80) and the title compound (830 mg) isolated as a white solid. $^1$H NMR (360 MHz, CDCl$_3$) δ 0.73 (3H, d, J=6.6 Hz), 0.79 (3H, d, J=6.6 Hz), 1.43–1.83 (12H, m), 2.06–2.20 (1H, m), 2.94–3.06 (1H, m), 3.43 (1H, dd, J=13.8 and 5 Hz), 4.27 (1H, dd, J=13.8 and 9.3 Hz), 5.10 (3H, m), 6.56 (1H, d, J=8.2 Hz), 7.24=7.35 (7H, m), 7.49 (1H, dd, J=8.4 and 8.4 Hz), 7.58 (1H, d, J=7.9 Hz). MS (CI, NH$_3$) 462 (M$^+$).

Step 2: 5-Cycloheptyl-1,3-dihydro-1-(2-methylpropyl)-3-(R,S)-[( 4-nitrophenyloxycarbonyl)amino]-2H-1,4-benzodiazepin-2-one 3(R,S)-[Benzyloxycarbonyl)amino]-5-cycloheptyl-1,3-dihydro-1-(2-methylpropyl)-2H-1,4-benzodiazepin-2-one (830 mg) was dissolved in hydrobromic acid (4 ml of a 30% solution in glacial acetic acid) and stirred at room temperature for 20 min. The yellow solution was then added dropwise to anhydrous diethyl ether (50 ml) at 0° C. and the resultant cream solid filtered off and washed with ether. The solid was partitioned between dichloromethane (50 ml) and 10% sodium hydroxide solution (50 ml). The organic layer was separated, dried (Na$_2$SO$_4$) and evaporated in vacuo to afford crude 3(R,S)-amino-5-cycloheptyl-1,3-dihydro-1-(2-methylpropyl)-2H-1,4-benzodiazepin-2-one as a viscous oil.

The amine was dissolved in anhydrous tetrahydrofuran (9 ml) under an atmosphere of nitrogen, at room temperature, and triethylamine (249 µl) was added dropwise. A solution of 4-nitrophenyl chloroformate (363 mg) in anhydrous tetrahydrofuran (9 ml) was then added, and the reaction mixture stirred for a further 2 h. After this time the undissolved solid was filtered off, washed with tetrahydrofuran, and the filtrate evaporated in vacuo. The residue was azeotroped with toluene (2×20 ml) and ether (20 ml). The resultant solid was then triturated in anhydrous ether to afford the title compound (420 mg) as a white solid. TLC (silica, petrol (60/80):ethyl acetate 2:1) Rf= 0.7. $^1$H NMR (360 MHz, CDCl$_3$) δ 0.77 (3H, d, J=6.6 Hz), 0.83 (3H, d, J=6.6 Hz), 1.40–1.87 (12H, m), 2.06–2.17 (1H, m), 2.98–3.02 (1H, m), 3.48 (1H, dd, J=13.8 and 5.0 Hz), 4.32 (1H, dd, J=13.8 and 9.3 Hz), 5.10 (1H, d, J=8.4 Hz), 6.92 (1H, d, J=8.2 Hz), 7.26–7.39 (4H, m), 7.53 (1H, dd, J=8.5 and 8.5 Hz), 7.61 (1H, m), 8.21 (2H, d, J=9 Hz).

Step 3: N-[3(R,S)-5-Cycloheptyl-2,3-dihydro-1-(2 -methylpropyl)-2-oxo-1H-1,4-benzodiazepin-3-yl]N'-[3-(N-methyl-N'-piperazinyl)phenyl]urea To a stirred solution of 5-cycloheptyl-1,3-dihydro-1-(2 -methylpropyl)-3(R,S)-[(4-nitrophenyloxycarbonyl)amino]-2H-1,4 -benzodiazepin-2-one (150 mg) in anhydrous dimethylformamide (3 ml), under an atmosphere of nitrogen, was added triethylamine (42 µl). After 5 min a solution of 1-amino-3-(N-methyl-N'-piperazinyl)benzene (64 mg) in anhydrous dimethylformamide (2 ml) was added and the solution heated at 50° C. for 1 h. The solvent was evaporated in vacuo and the residue partitioned between ethyl acetate (20 ml) and water (20 ml). The undissolved solid was filtered off, washed with ethyl acetate and water, then triturated with anhydrous diethyl ether to yield the desired urea (87 mg) as a white solid. $^1$H NMR (360 MHz, D$_6$-DMSO) δ 0.66 (3H, d, J=6.6 Hz), 0.77 (3H, d, J=6.6 Hz), 1.20–1.80 (12H, m), 1.96–2.10 (1H, m), 2.20 (3H, s), 2.18–2.20 (4H, m), 3.03–3.05 (4H, m), 3.14–3.18 (1H, m), 3.62 (1H, dd, J=13.9 and 4.4 Hz), 4.13 (1H, dd, J=13.9 and 9.6 Hz), 5.00 (1H, d, J=8.5 Hz), 6.49 (1H, d, J=8.3 Hz), 6.61 (1H, d, J=7.7 Hz), 7.03 (1H, t, J=8.1 Hz), 7.11 (1H, m), 7.23 (1H, d, J=7.7 Hz), 7.37 (1H, dd, J=7 and 7 Hz), 7.59–7.68 (2H, m), 7.78 (1H, d, J=6.8 Hz), 8.84 (1H, s). MS (FAB) 545 (M$^+$).

EXAMPLE 12

(+)-N-[5-Cycloheptyl-2,3-dihydro-1-methyl-2-oxo-1H-1,4-benzodiazepin-3-yl]
N'-[3-(N-methyl-N'-piperazinyl)phenyl]urea Step 1: (+)-3-[2((R)-Amino-3-phenylpropionylamino]-5-cycloheptyl-1,3-dihydro-1-methyl-2H-1,4-benzodiazepin-2-one To a solution of 3(R,S)-amino-5-cycloheptyl-1,3-dihydro-1-methyl-2H-1,4-benzodiazepin-2-one (4.08 g) in anhydrous dimethyl formamide (30 ml), under an atmosphere of nitrogen, was added in succession Boc-D-phenylalanine (3.98 g), 1-hydroxybenzotriazole trihydrate (2.03 g) and 1-ethyl-3-[3-(dimethylamino)propyl] carbodiimide hydrochloride (2.88 g). Triethylamine (2.09 ml) was then added and the resulting suspension stirred at ambient temperature for 1 h. The solvent was removed under reduced pressure and the residue partitioned between ethyl acetate (100 ml) and 10% citric acid solution (100 ml). The organic phase was separated and the aqueous phase extracted with ethyl acetate (3×50 ml). The combined organic phases were washed with 10% sodium hydroxide solution (100 ml), water (50 ml) and brine (50 ml). The organic layer was separated, dried ($Na_2SO_4$) and evaporated in vacuo to afford crude 3(R,S)-[2 (R)-(tert-butyloxycarbonyl)amino-3-phenylpropionylamino]-5-cycloheptyl-1,3-dihydro-1-methyl-2H-1,4-benzodiazepin-2-one.

3(R,S)-[ 2((R)-(tert-Butyloxycarbonyl)amino-3-phenylpropionylamino]-5-cycloheptyl-1,3-dihydro-1-methyl-2H-1,4-benzodiazepin-2-one (8.6 g) was dissolved in ethyl acetate (40 ml) and cooled to 0° C. This solution was then saturated with hydrogen chloride gas. After 1 h the resulting precipitate was removed by filtration (which was shown to be the undesired diastereoisomer (Rf=0.13, ethyl acetate)) and the filtrate evaporated. The solid residue was partitioned between ethyl acetate (25 ml) and 10% sodium carbonate solution (20 ml). The organic phase was separated and the aqueous layer extracted with ethyl acetate (2×25 ml). The combined organic phases were dried ($Na_2SO_4$) and evaporated in vacuo. The residue was chromatographed on silica gel using a gradient elution of 0→20% methanol in ethyl acetate to afford the title compound (2.5 g) as a yellow oil. $^1$H NMR (250 MHz, $CDCl_3$) δ 1.05–1.40 (4H, m), 1.52–1.70 (6H, m), 1.82–1.92 (1H, m), 2.02–2.10 (1H, m), 2.80–2.86 (1 m), 2.90–2.95 (1H, m), 3.20–3.40 (4H, m), 4.20 (1H, m), 5.30 (1H, d, J=8 Hz), 7.20–7.40 (7H, m), 7.41–7.60 (2H, m), 8.00–8.10 (1H, m). TLC (silica, ethyl acetate) Rf= 0.22. $[α]^{23}_D$=+28.0° C. (c=0.2, $CH_3OH$).

Step 2: 3-Amino-5-cycloheptyl-1,3-dihydro-1-methyl-2H-1,4-benzodiazepin-2-one (Enantiomer A)

A solution of (+)-3-[2(R)-amino-3-phenylpropionylamino]-5-cycloheptyl-1,3-dihydro-1-methyl-2H-1,4-benzodiazepin-2-one (2.5 g) in anhydrous dichloromethane (10 ml) was treated with phenyl isothiocyanate (0.76 ml), and then heated on the steam bath for 30 min. The solvent was evaporated in vacuo and the residue chromatographed on silica gel with 1:1 petrol (60/80):ethyl acetate as eluant to afford N-[1(R)-2-[(5-cycloheptyl-2,3-dihydro-1-methyl-2-oxo-1H-1,4-benzodiazepin-3-yl)amino]-2-oxo-1-(phenylmethyl)ethyl]N'-phenyl thiourea (2.3 g).

N-[ 1(R)-2-[(5-Cycloheptyl-2,3-dihydro-1-methyl-2-oxo-1H-1,4-benzodiazepin-3-yl)amino]-2-oxo-1-(phenylmethyl)ethyl]N'-phenyl thiourea (2.3 g) was dissolved in trifluoroacetic acid (10 ml), and stirred at room temperature for 30 min, then the solvent was removed under reduced pressure and the residue azeotroped with dichloromethane (2×20 ml) and toluene (2×20 ml). The residue was chromatographed on silica gel using 90:10:1.0:1.0 dichloromethane:methanol:acetic acid:water as the eluant to afford an orange gum. This was dissolved in ethyl acetate (80 ml), cooled to 0° C., and treated with 10% sodium carbonate solution (8 ml). After diluting with water (25 ml) and stirring for 1 min, the organic layer was separated and the aqueous phase re-extracted with ethyl acetate (2×50 ml). The combined organics were dried ($Na_2SO_4$) and evaporated in vacuo to afford the title compound (1.0 g) as a yellow oil. $^1$H NMR (250 MHz, $CDCl_3$) δ 1.20–1.70 (10H, m), 1.71–1.94 (1H, m), 1.95–2.13 (1H, m), 2.86–3.01 (1H, m), 3.40 (3H, s), 4.36 (1H, brs), 7.13–7.32 (2H, m), 7.41–7.57 (2H, m). TLC (silica, dichloromethane:methanol 9:1) Rf= 0.50.

Step 3: (+)-N-[5-Cycloheptyl-2,3-dihydro-1-methyl-2-oxo-1H-1,4-benzodiazepin-3-yl]N'[3-(N-methyl-N'-piperazinyl)phenyl]urea 1-Amino-3-(N-methyl-N'-piperazinyl)benzene (197 mg) in anhydrous tetrahydrofuran (30 ml) was cooled to 0° C. whereupon triphosgene (101 mg) was added. The mixture was stirred at 0° C. for 2 min, then triethylamine (430 µl) was added portionwise until pH8. The mixture was then stirred for a further 5 min, allowed to warm to 15° C., and then re-cooled to 0° C. Then a solution 3-amino-5-cycloheptyl-1,3-dihydro-1-methyl-2H-1,4 -benzodiazepin-2-one (200 mg) (Enantiomer A) in anhydrous tetrahydrofuran (10 ml) was added dropwise over 5 min. The mixture was stirred at 0° C. for 5 min, allowed to warm to room temperature and then stirred for a further 15 min. The undissolved material was removed by filtration. The filtrate was evaporated in vacuo and the residue partitioned between ethyl acetate (50 ml) and water (30 ml). The organic phase was separated, dried ($Na_2SO_4$) and evaporated. The residue was chromatographed on silica gel with dichloromethane:methanol (9:1) as eluant to afford the title compound (239 mg) as a colourless solid. Mp 160° C. (dec.). $^1$H NMR (250 MHz, D6-DMSO) δ 1.05–1.87 (11H, m), 1.88–2.04 (1H, m) 2.21 (3H, s), 2.36–2.47 (4H, m), 2.95–3.21 (5H, m), 3.36 (3H, s), 5.05 (1H, d, J=8 Hz), 6.50 (1H, dd, J=8.2 and 2.0 Hz), 6.61 (1H, d, J=8 Hz), 7.04 (1H, t, J=7.5 Hz), 7.13 (1H, s), 7.25 (1H, d, J=7.5 Hz), 7.39 (1H, t, J=7.0 Hz), 7.52–7.70 (2H, m), 7.76 (1H, d, J=8.0 Hz), 8.89 (1H, s).

EXAMPLE 13

N-[3(R,S)-5-Cyclohexyl-2,3-dihydro-1-methyl-2-oxo-1H-1,4-benzodiazepin-3-yl]N'-3-(N-morpholinomethyl)phenyl]urea Step 1: 3(R,S)-[(Benzyloxycarbonyl)amino]-5-cyclohexyl-1,3-dihydro-1-methyl-2H-1,4-benzodiazepin-2-one A solution of 3(R,S)-[(benzyloxycarbonyl)amino]-5-cyclohexyl-1,3-dihydro-2H-1,4-benzodiazepin-2-one (1.1 g) in dimethylformamide (13 ml), under an atmosphere of nitrogen, was treated with sodium hydride (117 mg of a 55–60% dispersion in mineral oil) in one portion, at –10° C. After 30 min at –10° C., iodomethane (174 µl) was added in one portion and the solution allowed to reach 0° C. over 1 h. The solvent was then removed in vacuo and the crude residue partitioned between water (100 ml) and dichloromethane (100 ml). The organic phase was separated and the aqueous phase extracted with dichloromethane (2×100 ml). The combined organic layers were washed with brine, dried ($MgSO_4$) and evaporated. The residue was chromatographed on silica, using 1:1 petrol:ethyl acetate as the eluant, to afford the title compound (0.75 g) as a white solid. Mp 205°–207° C. $^1$H NMR (360 MHz, CDCl$_3$) δ 1.03–2.04 (10H, m), 2.76 (1H, m), 3.36 (3H, s), 5.10 (3H, m), 6.52 (1H, d, J=8 Hz), 7.25–7.55 (9H, m).

Step 2: 3(R,S)-Amino-5-cyclohexyl-1,3-dihydro-1-methyl-2H-1,4-benzodiazepin-2-one A mixture of 3(R,S)-[(benzyloxycarbonyl)amino]-5-cyclohexyl-1,3-dihydro-1-methyl-2H-1,4-benzodiazepin-2-one (3.0 g) and hydrobromic add (45% in acetic acid, 6.2 ml) was stirred for 1 h at room temperature under an atmosphere of nitrogen. The mixture was then diluted with cold anhydrous diethyl ether (40 ml) and it was stirred at 0° C. for 45 min. The white precipitate was collected by filtration, washed with cold diethyl ether (4×30 ml) and then dissolved in a mixture of water (30 ml) and aqueous sodium hydroxide (2M, 15 ml). The basic aqueous phase was extracted with ethyl acetate (3×70 ml) and the combined organic layers were washed with brine (30 ml), dried (Na$_2$SO$_4$) and concentrated. The residue was chromatographed on silica gel using 94:6, dichloromethane:methanol as the eluant, to afford the title compound (1.6 g). Mp 133°–136° C. $^1$H NMR (360 MHz, CDCl$_3$) δ 1.02–1.40 (4H, m), 1.47–1.56 (1H, m), 1.61–1.74 (3H, m), 1.84–1.91 (1H, m), 1.96–2.06 (1H, m), 2.17 (2H, brs), 2.70–2.80 (1H, m), 3.39 (3H, s), 4.29 (1H, s), 7.20–7.27 (2H, m), 7.44–7.54 (2H, m).

Step 3: N-[3(R,S)-5-Cyclohexyl-2,3-dihydro-1-methyl-2-oxo-1H-1,4-benzodiazepin-3-yl]N'-[3-(N-morpholinomethyl)phenyl]urea 1-Amino-3-(N-morpholinomethyl)benzene (54 mg) in anhydrous tetrahydrofuran (8 ml) was cooled to 0° C. whereupon triphosgene (27 mg) was added. The mixture was stirred at 0° C. for 2 min, then triethylamine (114 μl) was added portionwise until pH8. The mixture was then stirred for a further 5 min, allowed to warm to 15° C., and then re-cooled to 0° C. Then a solution of 3(R,S)-amino-5-cyclohexyl-1,3-dihydro-1-methyl-2H-1,4-benzodiazepin-2-one (59 mg) in anhydrous tetrahydrofuran (8 ml) was added dropwise over 5 min. The mixture was stirred at 0° C. for 5 min, allowed to warm to room temperature and then stirred for a further 30 min. The undissolved material was removed by filtration. The solvent was evaporated in vacuo and the residue partitioned between ethyl acetate (30 ml) and water (20 ml). The organic phase was separated, dried (Na$_2$SO$_4$) and evaporated. The crude solid was recrystallised from ethyl acetate to afford the title compound as a colourless solid (50 mg). $^1$H NMR (250 MHz, D$_6$-DMSO) δ 0.80–1.70 (8H, m), 1.72–1.84 (1H, m), 1.85–2.00 (1H, m), 2.24–2.39 (4H, m), 2.84–3.01 (1H, m), 3.32 (3H, s), 3.36 (2H, s), 3.49–3.63 (4H, m), 5.06 (1H, d, J=10 Hz), 6.85 (1H, d, J=10 Hz), 7.10–7.30 (3H, m), 7.32–7.40 (2H, m), 7.50–7.72 (2H, m), 7.78 (1H, d, J=8 Hz), 8.98 (1H, s). TLC (silica, dichloromethane:methanol 9:1) Rf= 0.65.

EXAMPLE 14

N-[3(R)-Cyclohexyl-2,3-dihydro-1-methyl-2-oxo-1H-1,4-benzodiazepin-3-yl]N'-[3=(N-morpholinomethyl)phenyl]urea 1-Amino-3-(N-morpholinomethyl)benzene (270 mg) in anhydrous tetrahydrofuran (40 ml) was cooled to 0° C. whereupon triphosgene (134 mg) was added. The mixture was stirred at 0° C. for 2 min, then triethylamine (570 μl) was added portionwise until pH8. The mixture was then stirred for a further 5 min, allowed to warm to 10° C., and then re-cooled to 0° C. Then a solution of 3(R)-amino-5-cyclohexyl-1,3-dihydro-1-methyl-2H-1,4-benzodiazepin-2-one (250 mg) in anhydrous tetrahydrofuran (10 ml) was added dropwise over 5 min. The mixture was stirred at 0° C. for 5 min, allowed to warm to room temperature and then stirred for a further 1 h. The undissolved material was removed by filtration. The solvent was evaporated in vacuo and the residue partitioned between ethyl acetate (50 ml) and water (30 ml). The organic phase was separated, dried (Na$_2$SO$_4$) and evaporated. The crude solid was chromatographed on silica gel using a gradient elution of 0→5% methanol in dichloromethane to afford the title compound (225 mg). Mp 155° C. (dec.). $^1$H NMR (250 MHz, D$_6$-DMSO) δ 0.80–1.70 (8H, m), 1.72–1.84 (1H, m), 1.85–2.00 (1H, m), 2.24–2.39 (4H, m), 2.84–3.01 (1H, m), 3.32 (3H, s), 3.36 (2H, s), 3.49–3.63 (4H, m), 5.06 (1H, d, J=10 Hz), 6.85 (1H, d, J=10 Hz), 7.10–7.30 (3H, m), 7.32–7.40 (2H, m), 7.50–7.72 (2H, m), 7.78 (1H, d, J=8 Hz), 8.98 (1H, s).

EXAMPLE 15

N-[3(R,S)-5-Cyclohexyl-2,3-dihydro-1-methyl-2-oxo-1H-1,4,-benzodiazepin-3-yl]N'-[4-(N-morpholinomethyl)phenyl]urea Step 1: 4-(N-Morpholinomethyl)-1-nitrobenzene A solution of morpholine (2.0 g) in anhydrous acetone (100 ml) was treated with potassium carbonate (4.8 g) and 4-nitrobenzyl bromide (5.0 g). The mixture was stirred at room temperature for 16 h. The solvent was evaporated and the residue partitioned between ethyl acetate (50 ml) and water (50 ml). The aqueous layer was washed with ethyl acetate (2×80 ml). The combined organics were dried (Na$_2$SO$_4$), evaporated and the residue was chromatographed on silica gel with petrol:ethyl acetate (1:1) as the eluant, to afford the title compound (3.8 g). Mp 82°–84° C. $^1$H NMR (360 MHz, CDCl$_3$) δ 2.45–2.47 (4H, m), 3.51 (2H, s), 3.67–3.77 (4H, m), 7.52 (2H, d, J=8.7 Hz), 8.19 (2H, d, J=8.7 Hz).

Step 2: 1-Amino-4-(N-morpholinomethyl)benzene 4-(N-Morpholinomethyl)-1-nitrobenzene (2.00 g) in ethanol (150 ml) was treated with 10% palladium on carbon (200 mg, 10% (w/w)). The mixture was hydrogenated at 25 psi for 4 min. The catalyst was filtered off and the solvent evaporated. The residue was chromatographed on silica gel, with ethyl acetate as eluant, to afford the title compound (800 mg). Mp 106°–108° C. $^1$H NMR (250 MHz, CDCl$_3$) δ 2.42–2.66 (4H, m), 3.52 (2H, s), 3.78 (2H, brs), 3.80–3.91 (4H, m), 6.72–6.84 (2H, d, J=8.4 Hz), 7.16–7.28 (2H, d, J=8.4 Hz).

Step 3: 5-Cyclohexyl-1,3-dihydro-1-methyl-3(R,S)-[(4-nitrophenyloxycarbonyl)amino]-2H-1,4-benzodiazepin-2-one A solution of 3(R,S)-amino-5-cyclohexyl-1,3-dihydro-1-methyl-2H-1,4-benzodiazepin-2-one (1.0 g) in anhydrous tetrahydrofuran (20 ml) under an atmosphere of nitrogen at 0° C. was treated with triethylamine (0.51 ml), followed by a solution of 4-nitrophenyl chloroformate (0.75 g) in anhydrous tetrahydrofuran (10 ml) dropwise. After stirring at ambient temperature for 20 min, the solid which precipitated from the mixture was filtered and the filtrate was evaporated in vacuo. The residue was triturated with diethyl ether to give the title compound (1.2 g, 75%) as a colourless solid. Mp 165°–168° C. $^1$H NMR (360 MHz, CDCl$_3$) δ 1.05 (1H, m), 1.18–1.42 (3H, m), 1.55 (1H, m), 1.65 (3H, m), 1.87 (1H, m), 2.05 (1H, m), 2.80 (1H, m), 3.43 (3H, s), 5.18 (1H, d, J=8.3 Hz), 6.90 (1H, d, J=8.2 Hz), 7.30 (4H, m), 7.57 (2H, m), 8.23 (2H, d, J=7.1 Hz).

Step 4: N-[3(R,S)-5-Cyclohexyl-2,3-dihydro-1-methyl-2-oxo-1H-1,4-benzodiazepin-3-yl]N'-[4-(N-morpholinomethyl)phenyl]urea A solution of 5-cyclohexyl-1,3-dihydro-1-methyl-3(R,S)-[(4-nitrophenyloxycarbonyl)amino]-2H-1,4-benzodiazepin-2-one (200 mg) in anhydrous dimethylformamide (8 ml), under an atmosphere of nitrogen, was treated with triethylamine (63 µl). This mixture was stirred at room temperature for 5 min whereupon a solution of 1-amino-4-(N-morpholinomethyl)benzene (88 mg) in anhydrous dimethylformamide (4 ml) was added dropwise over 5 min. The mixture was heated to 50° C. and stirred for 5 h. The solvent was evaporated and the residue partitioned between ethyl acetate (50 ml) and water (50 ml). The organic phase was separated, dried ($Na_2SO_4$) and evaporated in vacuo. The crude solid was recrystallised from ethyl acetate to afford the title compound (75 mg) as a colourless solid. Mp 170°–172° C. $^1$H NMR (360 MHz, $CDCl_3$) δ 0.96–1.75 (8H, m), 1.77–1.90 (1H, m), 1.96–2.07 (1H, m), 2.37–2.48 (4H, m), 2.72–2.83 (1H, m), 3.40 (3H, s), 3.43 (2H, s), 3.65–3.76 (4H, m), 5.38 (1H, d, J=8.0 Hz), 6.63 (1H, d, J=8.1 Hz), 6.65 (1H, s), 7.20–7.34 (6H, m), 7.46–7.60 (2H, m).

EXAMPLE 16

N-[3(R,S)-5-Cyclohexyl-2,3-dihydro-1-methyl-2-oxo-1H-1,4,-benzodiazepin-3-yl]N'-[2-(N-morpholinomethyl)phenyl]urea Step 1: 1-Amino-2-(N-morpholinomethyl)benzene A solution of morpholine (2.0 g) in anhydrous acetone (100 ml) was treated with potassium carbonate (4.8 g) and 2-nitrobenzyl bromide (5.0 g). The mixture was stirred at room temperature for 16 h. The solvent was evaporated and the residue partitioned between ethyl acetate (50 ml) and water (50 ml). The aqueous layer was washed with ethyl acetate (2×50 ml). The combined organics were dried ($Na_2SO_4$) and evaporated to afford crude 2-(N-morpholinomethyl)-1-nitrobenzene (3.5 g).

2-(N-Morpholinomethyl)-1-nitrobenzene (2.0 g) in ethanol (150 ml) was treated with 10% palladium on carbon (200 mg, 10% (w/w)). The mixture was hydrogenated at 25 psi for 10 min. The catalyst was filtered off and the solvent evaporated. The residue was chromatographed on silica gel with petrol (60/80):ethyl acetate (2:1) as the eluant to afford the title compound (1.29 g) as colourless needles. Mp 72°–73° C. $^1$H NMR (250 MHz, $CDCl_3$) δ 2.36–2.50 (4H, m), 3.53 (2H, s), 3.65–3.77 (4H, m), 6.62–6.73 (2H, m), 6.96–7.14 (2H, m).

Step 2: N-[3(R,S)-5-Cyclohexyl-2,3-dihydro-1-methyl-2-oxo-1H-1,4-benzodiazepin-3-yl]N'-[2-(N-morpholinomethyl)phenyl]urea A solution of 5-cyclohexyl-1,3-dihydro-1-methyl-3(R,S)-[(4-nitrophenyloxycarbonyl)amino]-2H-1,4-benzodiazepin-2-one (200 mg) in anhydrous dimethylformamide (8 ml), under an atmosphere of nitrogen, was treated with triethylamine (63 µl). This mixture was stirred at room temperature for 5 min whereupon a solution of 1-amino-2-(N-morpholinomethyl)benzene (88 mg) in anhydrous dimethylformamide (4 ml) was added dropwise over 5 min. The mixture was heated to 50° C. and stirred for 3 h. The solvent was evaporated and the residue was partitioned between ethyl acetate (50 ml) and water (50 ml). The organic phase was separated, dried ($Na_2SO_4$) and evaporated in vacuo. The crude solid was recrystallised from ethyl acetate to afford the title compound (110 mg). Mp 168° C. $^1$H NMR (360 MHz, $CDCl_3$) δ 1.00–1.10 (1H, m), 1.11–1.44 (3H, m), 1.50–1.75 (4H, m), 1.80–1.92 (1H, m), 2.00–2.10 (1H, m), 2.42–2.60 (4H, m), 2.73–2.86 (1H, m), 3.41 (3H, s), 3.52–3.68 (2H, m), 3.70–3.90 (4H, m), 5.39 (1H, d, J=8.1 Hz), 6.33 (1H, d, J=7.9 Hz), 6.91 (1H, t, J=7.2 Hz), 7.06 (1H, d, J=6.8 Hz), 7.20–7.34 (3H, m), 7.46–7.60 (2H, m), 7.97 (1H, d, J=8.2 Hz), 9.69 (1H, s).

EXAMPLE 17

N-[3(R,S)-5-Cyclohexyl-2,3-dihydro-2-oxo-1-propyl-1H-1,4-benzodiazepin-3-yl]N'-[3-(N-morpholinomethyl)phenyl]urea 1-Amino-3-(N-morpholinomethyl)benzene (236 mg) in anhydrous tetrahydrofuran (40 ml) was cooled to 0° C. whereupon triphosgene (120 mg) was added. The mixture was stirred at 0° C. for 2 min, then triethylamine (513 µl) was added portionwise until pH8. The mixture was then stirred for a further 5 min, allowed to warm to 10° C., and then recooled to 0° C. Then a solution of 3(R,S)-amino-5-cyclohexyl-1,3-dihydro-1-propyl-2H-1,4-benzodiazepin-2-one (250 mg) in anhydrous tetrahydrofuran (10 ml) was added dropwise over 5 min. The mixture was stirred at 0° C. for 5 min, allowed to warm to room temperature and then stirred for a further 2 h. The solvent was evaporated in vacuo and the residue partitioned between ethyl acetate (50 ml) and water (20 ml). The organic phase was separated, dried ($Na_2SO_4$) and evaporated. The crude solid was chromatographed on silica gel with dichloromethane:methanol (99:1) as the eluant to afford the title compound (216 mg). Mp 230° C. $^1$H NMR (360 MHz, $CDCl_3$) δ 0.82 (3H, t, J=7.4 Hz), 1.00–1.90 (11H, m), 1.99–2.10 (1H, m), 2.40–2.52 (4H, m), 2.74–2.86 (1H, m), 3.46 (2H, s), 3.50–3.62 (1H, m), 3.66–3.76 (4H, m), 4.26–4.38 (1H, m), 5.33 (1H, d, J=7.9 Hz), 6.66 (1H, d, J=8.0 Hz), 6.83 (1H, s), 7.00 (1H, d, J=6.5 Hz), 7.16–7.42 (5H, m), 7.45–7.60 (2H, m).

EXAMPLE 18

N-[3(R,S)-5-Cycloheptyl-2,3-dihydro-1-methyl-2-oxo-1H-1,4-benzodiazepin-3-yl]N'-[3-(N-methyl-N'-piperazinyl) phenyl]urea Step 1: 5-Cycloheptyl-1,3-dihydro-1-methyl-3(R,S)-[(4-nitrophenyloxycarbonyl)amino]-2H-1,4-benzodiazepin-2-one 3(R,S)-[Benzyloxycarbonyl)amino]-5-cycloheptyl-1,3-dihydro-1-methyl-2H-1,4-benzodiazepin-2-one (0.67 g) was dissolved in hydrobromic add (4 ml of a 30% solution in glacial acetic add) and stirred at room temperature for 20 min. The yellow solution was then added dropwise to anhydrous diethyl ether (20 ml) at 0° C. and the resultant cream solid filtered off and washed with ether. The solid was partitioned between dichloromethane (50 ml) and 10% sodium hydroxide solution (50 ml). The organic layer was separated, dried ($Na_2SO_4$) and evaporated in vacuo to afford crude 3(R,S)-amino-5-cycloheptyl-1,3-dihydro-1-methyl-2H-1,4-benzodiazepin-2-one as a colourless viscous oil.

The amine was dissolved in anhydrous tetrahydrofuran (9 ml) under an atmosphere of nitrogen, at room temperature, and triethylamine (221 µl) was added dropwise. A solution of 4-nitrophenyl chloroformate (322 mg) in anhydrous tetrahydrofuran (9 ml) was then added, and the reaction mixture stirred for a further 3 h. After this time the undissolved solid was filtered off, washed with tetrahydrofuran, and the filtrate evaporated in vacuo. The residue was azeotroped with toluene (2×50 ml) and the residue triturated with anhydrous ether to afford the title compound (425 mg) as a white solid. TLC (silica, petrol (60/80):ethyl acetate 2:1). Rf= 0.3. $^1$H NMR (360 MHz, CDCl$_3$) δ 1.22–2.10 (12H, m), 2.98 (1H, m), 3.45 (3H, s), 5.15 (1H, d, J=8.2 Hz), 6.89 (1H, d, J=9.2 Hz), 7.26–7.35 (4H, m), 7.49–7.60 (2H, m), 8.22 (2H, d, J=7.1 Hz).

Step 2: N-[3(R,S)-5-Cycloheptyl-2,3-dihydro-1-methyl-2-oxo-1H-1,4-benzodiazepin-3-yl]N'-[3-(N-methyl-N'-piperazinyl)phenyl]urea To a stirred solution of 5-cycloheptyl-1,3-dihydro-1-methyl-3(R,S)-[(4-nitrophenyloxycarbonyl)amino]-2H-1,4-benzodiazepin-2-one (200 mg) in anhydrous dimethylformamide (5 ml), under an atmosphere of nitrogen, was added triethylamine (61 µl). After 2 min a solution of 1-amino-3-(N-methyl-N'-piperazinyl)benzene (85 mg) in anhydrous dimethylformamide (5 ml) was added and the solution heated at 50° C. for 1.5 h. After this time the solvent was evaporated in vacuo and the residue partitioned between ethyl acetate (20 ml) and water (20 ml). An undissolved solid was filtered off and triturated with anhydrous diethyl ether to give the desired urea (128 mg) as a white solid. $^1$H NMR (360 MHz, D$_6$-DMSO) δ 1.13–1.94 (12H, m), 2.19 (3H, s), 2.40–2.43 (4H, m), 3.03–3.12 (5H, m), 3.30 (3H, s), 5.04 (1H, d, J=8.4 Hz), 6.49 (1H, dd, 8.1 and 1 Hz), 6.62 (1H, d, J=9.0 Hz), 7.03 (1H, t, J=8.1 Hz), 7.12 (1H, m), 7.22 (1H, d, J=8.4 Hz), 7.38 (1H, dd, J=7.6 and 7.6 Hz), 7.54 (1H, d, J=7.7 Hz), 7.63 (1H, dd, J=8.3 and 8.3 Hz), 7.76 (1H, d, J=7.6 Hz), 8.86 (1H, s). MS (CI, NH$_3$) 502 (M$^+$).

We claim:

1. A compound of the Formula (I):

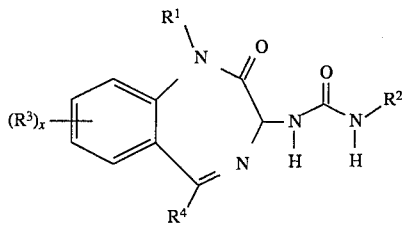

wherein:

R$^1$ represents H, C$_{1-6}$alkyl, C$_{3-7}$cycloalkyl, cyclopropylmethyl, CH$_2$CO$_2$R$^5$ (where R$^5$ is C$_{1-4}$alkyl), CH$_2$CONR$^6$R$^7$ (where R$^6$ and R$^7$ each independently represents H or C$_{1-4}$alkyl, or R$^6$ and R$^7$ together form a chain (CH$_2$)$_p$ where p is 4 or 5), C$_{1-6}$alkylNR$^8$R$^9$ or C$_{-6}$alkylCONR$^8$R$^9$ where R$^8$ and R$^9$ together with the nitrogen atom to which they are attached form a 5 to 8 membered non-aromatic ring system containing a second heteroatom selected from O, S or NR$^{10}$, where R$^{10}$ is H or C$_{1-4}$alkyl;

R$^2$ represents a phenyl or pyridyl group optionally substituted by one or more substituents selected from C$_{1-6}$alkyl, halo, hydroxy, C$_{1-4}$alkoxy, (CH$_2$)$_q$-tetrazolyl optionally substituted in the tetrazole ring by C$_{1-4}$alkyl, (CH$_2$)$_q$-imidazoyl, (CH$_2$)$_q$-triazolyl (where q is 0, 1, 2 or 3), 5-hydroxy-4-pyrone, NR$^6$R$^7$, NR$^{10}$COR$^5$, NR$^{10}$CONR$^{10'}$R$^5$ (where R$^{10}$ and R$^{10'}$ are each independently H or C$_{1-4}$alkyl and R$^5$ is as previously defined), CONR6R$^7$ (where R$^6$ and R$^7$ are as previously defined), SO(C$_{1-6}$alkyl), SO$_2$(C$_{1-6}$alkyl), trifluoromethyl, CONHSO$^2$R$^{11}$, SO$_2$NHCOR$^{11}$ (where R$^{11}$ is C$_{1-6}$alkyl, optionally substituted aryl wherein said substituents are selected from C$_{1-4}$alkyl, C$_{1-4}$alkoxy, halo and trifluoromethyl, 2,2-difluorocyclopropane or trifluoromethyl), SO$_2$NHR$^{12}$ (where R$^{12}$ is a nitrogen containing heterocycle selected from thiazole, thiadiazole, and pyrazine), B(OH)$_2$ or (CH$_2$)$_q$CO$_2$H, where q is as previously defined; or R$^2$ represents a group

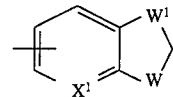

where X$^1$ represents CH or N; W represents CH$_2$ or NR$^{10}$, where R$^{10}$ is as previously defined, and W$^1$ represents CH$^2$, or W and W$^1$ each represent O; or R$^2$ represents phenyl substituted by a group

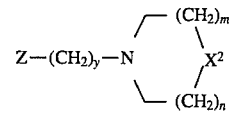

wherein X$^2$ is O, S or NR$^{10}$, where R$^{10}$ is as previously defined; Z is a bond, O or S; m is 1, 2 or 3; n is 1, 2 or 3; and y is 0, 1, 2 or 3;

Each R$^3$ represents C$_{1-6}$alkyl, halo or NR$^6$R$^7$, where R$^6$ and R$^7$ are as previously defined;

R$^4$ represents bridged C$_{6-10}$bicycloalkyl or C$_{3-7}$cycloalkyl optionally substituted by one or more C$_{1-4}$alkyl groups;

x is 0, 1, 2 or 3;

with the proviso that when R$^1$ is H, C$_{1-6}$alkyl, C$_{3-7}$cycloalkyl, cyclopropylmethyl, CH$_2$CO$_2$R$^5$ or CH$_2$CONR$^6$R$^7$, R$^2$ represents phenyl substituted by

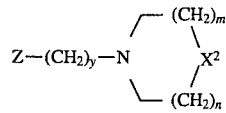

and pharmaceutically acceptable salts thereof.

2. A compound as claimed in claim 1 wherein R$^1$ is C$_{1-6}$alkyl, C$_{3-7}$ cycloalkyl, cyclopropylmethyl, CH$_2$CO$_2$R$^5$ or CH$_2$CONR$^6$R$^7$; R$^2$ is phenyl substituted by a group:

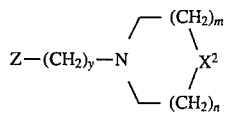

wherein X$^2$, Z, m, n and y are as previously defined; and R$^4$ represents C$_{3-7}$cycloalkyl.

3. A compound as claimed in claim 1 wherein R$^1$ is C$_{1-6}$ alkyl NR$^8$R$^9$ or C$_{1-6}$ alkyl CONR$^8$R$^9$; R$^2$ is a phenyl group optionally substituted by one or more of C$_{1-6}$alkyl, halo, hydroxy, C$_{1-4}$alkoxy, (CH$_2$)$_q$-tetrazolyl optionally substituted in the tetrazole ring by C$_{1-4}$alkyl, (CH$_2$)$_q$ -imidazolyl, (CH$_2$)$_q$-triazolyl, 5-hydroxy-4-pyrone, NR$^6$R$^7$, CONR$^6$R$^7$, NR$^{10}$COR$^{11}$, NR$^{10}$CONR$^{10'}$R$^5$, SO(C$_{1-6}$alkyl), SO$_2$(C$_{1-6}$alkyl), trifluoromethyl, CONHSO$_2$R$^{11}$, SO$_2$NHCOR$^{11}$, SO$_2$NHCOR$^{11}$, SO$_2$NHR$^{12}$, B(OH)$_2$, (CH$_2$)$_q$CO$_2$H; or R$^2$ represents a group

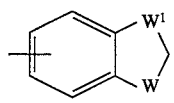

where W and W' are as previously defined.

4. A compound of the formula (Ia):

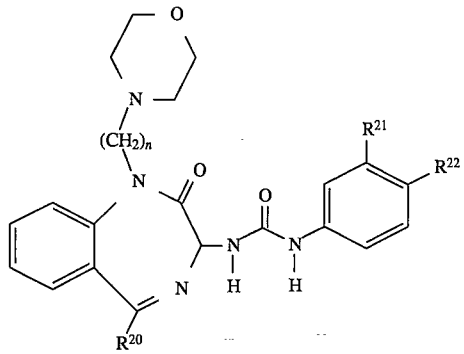

wherein $R^{20}$ is $C_{4-7}$cycloalkyl;

$R^{21}$ is $C_{1-4}$alkyl and $R^{22}$ is H, or $R^{21}$ and $R^{22}$ together form a chain $(CH_2)_3$;

n is 2 or 3;

and salts thereof.

5. A compound of the formula (Ib):

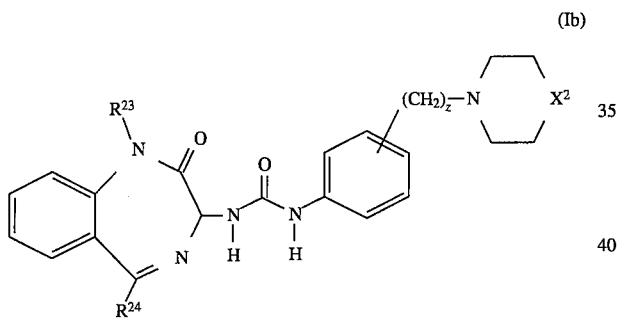

wherein $X^2$ is as defined in claim 1 for formula (I);

$R^{23}$ is $C_{1-6}$alkyl;

$R^{24}$ is cyclopentyl, cyclohexyl or cycloheptyl;

z is 0 or 1;

and salts thereof.

6. A compound selected from

N-[ 3 (R,S) -5-Cycloheptyl-2,3-dihydro-1-(2 -(N-morpholino)ethyl)-2-oxo-1H-1,4-benzodiazepin-3-yl] N-[3-methylphenyl] urea N-[ 3(R,S) -5-Cyclohexyl-2,3-dihydro-1-(2-(N- morpholino)ethyl)-2-oxo-1H-1,4-benzodiazepin-3-yl] N-[ 3-methylphenyl] urea N-[ 3(R,S) -5-Cyclohexyl-2,3-dihydro-1-(2 -(N-morpholino)ethyl)-2-oxo-1H-1,4-benzodiazepin-3-yl] N-[ 5-indanyl] urea N-[3(R,S)5-Cyclohexyl-2,3-dihydro-2-oxo-1 -propyl-1H-1,4-benzodiazepin-3-yl] N-[4 -(N-piperazinyl)phenyl]urea N-[ 3(R,S)-5-Cyclohexyl-2,3-dihydro-2-oxo-1 -propyl-1H-1,4-benzodiazepin-3-yl] N-[ 4-(N-methyl-N-piperazinyl)phenyl] urea N-[ 3(R,S)-5-Cyclohexyl-2,3-dihydro-2-oxo-1 -propyl-1H-1,4-benzodiazepin-3-yl] N-[ 3-(N-methyl-N-piperazinyl)phenyl]urea N-[ 3(R,S)-2,3-Dihydro-1-methyl-5-(4-methylpiperidin-1-yl)-2-oxo-1H-1,4-benzodiazepin-3-yl] N-[3-(N-methyl-N-piperazinyl)phenyl]urea N-[ 3(R,S)-5-Cycloheptyl-2,3-dihydro-1-methyl-2-oxo-1H-1,4-benzodiazepin-3-yl]N-[ 3 -(N-morpholinomethyl)phenyl] urea N-(R,S)-5-Cycloheptyl-2,3-dihydro-1-methyl-2 -oxo-1H-1,4-benzodiazepin-3-yl]N-[3-(2 -(N-morpholino)ethoxy)phenyl]urea N-[3(R)-5-Cyclohexyl-2,3-dihydro-1-methyl-2 -oxo-1H-1,4-benzodiazepin-3-yl]N-[3-(2 -(N-morpholino)ethoxy)phenyl]urea N-[ 3(R,S)-5-Cycloheptyl-2,3-dihydro-1 -(2-methylpropyl)-2-oxo-1H-1,4-benzodiazepin-3-yl] N-[ 3-(N-methyl-N-piperazinyl)phenyl]urea (+)-N-[ 5-Cycloheptyl-2,3-dihydro-1-methyl-2 -oxo-1H-1,4-benzodiazepin-3-yl] N-[ 3-(N-methyl-N-piperazinyl)phenyl]urea N-[3(R,S)-5-Cyclohexyl-2,3-dihydro-1-methyl-2 -oxo-1H-1,4-benzodiazepin-3-yl]N-3 -(N-morpholinomethyl)phenyl]urea N-[ 3(R) -Cyclohexyl-2,3-dihydro-1-methyl-2-oxo-1H-1,4-benzodiazepin-3-yl] N-[ 3 -(N-morpholinomethyl)phenyl]urea N-[3(R,S)-5-Cyclohexyl-2,3-dihydro-1-methyl-2 -oxo-1H-1,4-benzodiazepin-3-yl]N-[4 -(N-morpholinomethyl)phenyl]urea N-[ 3(R,S)-5-Cyclohexyl-2,3-dihydro-1-methyl-2 -oxo-1H-1,4-benzodiazepin-3-yl] N-[2 -(N-morpholinomethyl)phenyl]urea N-[ 3 (R,S)-5-Cyclohexyl-2,3-dihydro-2-oxo-1-propyl-1H-1,4-benzodiazepin-3-yl]N-[ 3 -(N-morpholinomethyl)phenyl] urea N-[3(R,S)-5-Cycloheptyl-2,3-dihydro-1-methyl-2 -oxo-1H-1,4-benzodiazepin-3-yl]N-[3-(N-methyl-N-piperazinyl)phenyl]urea or pharmaceutically acceptable salts thereof.

7. A pharmaceutical composition which comprises a compound of the formula (I) as defined in claim 1 or a pharmaceutically acceptable salt thereof in association with a carrier therefor.

* * * * *